(12) United States Patent
Williams

(10) Patent No.: US 11,259,812 B2
(45) Date of Patent: Mar. 1, 2022

(54) ANVIL ASSEMBLY DELIVERY SYSTEMS

(71) Applicant: Covidien LP, Mansfield, MA (US)

(72) Inventor: Justin Williams, Naugatuck, CT (US)

(73) Assignee: Covidien LP, Mansfield, MA (US)

( * ) Notice: Subject to any disclaimer, the term of this patent is extended or adjusted under 35 U.S.C. 154(b) by 270 days.

(21) Appl. No.: 16/678,232

(22) Filed: Nov. 8, 2019

(65) Prior Publication Data

US 2020/0078021 A1  Mar. 12, 2020

Related U.S. Application Data

(60) Continuation of application No. 15/831,679, filed on Dec. 5, 2017, now Pat. No. 10,470,772, which is a division of application No. 14/313,303, filed on Jun. 24, 2014, now Pat. No. 9,861,367.

(51) Int. Cl.

| | |
|---|---|
| *A61B 17/064* | (2006.01) |
| *A61B 17/115* | (2006.01) |
| *A61B 17/11* | (2006.01) |
| *A61B 17/068* | (2006.01) |
| *A61B 17/00* | (2006.01) |
| *A61B 17/072* | (2006.01) |

(52) U.S. Cl.
CPC ........ *A61B 17/1155* (2013.01); *A61B 17/068* (2013.01); *A61B 17/1114* (2013.01); *A61B 2017/00367* (2013.01); *A61B 2017/00473* (2013.01); *A61B 2017/07257* (2013.01)

(58) Field of Classification Search
CPC .. A61B 17/068; A61B 17/115; A61B 17/1155
USPC ............. 227/175.1, 176.1; 289/1.2, 1.5, 18.1
See application file for complete search history.

(56) References Cited

U.S. PATENT DOCUMENTS

| | | | |
|---|---|---|---|
| 3,193,165 A | 7/1965 | Akhalaya et al. |
| 3,388,847 A | 6/1968 | Kasulin et al. |
| 3,552,626 A | 1/1971 | Astafiev et al. |
| 3,638,652 A | 2/1972 | Kelley |
| 3,738,692 A | 6/1973 | Martuch |
| 3,771,526 A | 11/1973 | Rudie |
| 4,198,982 A | 4/1980 | Fortner et al. |
| 4,207,898 A | 6/1980 | Becht |
| 4,221,024 A | 9/1980 | Becker |

(Continued)

FOREIGN PATENT DOCUMENTS

| | | |
|---|---|---|
| CA | 908529 A | 8/1972 |
| DE | 1057729 B | 5/1959 |

(Continued)

OTHER PUBLICATIONS

Partial European Search Report issued in corresponding EP 15173264 dated Nov. 9, 2015.

(Continued)

*Primary Examiner* — Eyamindae C Jallow
(74) *Attorney, Agent, or Firm* — Carter, DeLuca & Farrell LLP

(57) ABSTRACT

An anvil assembly suitable for trans-oral delivery includes an anvil head configured to receive a retrieval suture that is separable from the anvil head following delivery of the anvil assembly. An anvil delivery assembly includes the anvil assembly, a delivery assembly secured to the anvil assembly, and a retrieval suture selectively secured to the anvil assembly for retrieving the anvil assembly.

13 Claims, 19 Drawing Sheets

(56) References Cited

U.S. PATENT DOCUMENTS

| | | |
|---|---|---|
| 4,289,133 A | 9/1981 | Rothfuss |
| 4,304,236 A | 12/1981 | Conta et al. |
| 4,319,576 A | 3/1982 | Rothfuss |
| 4,350,160 A | 9/1982 | Kolesov et al. |
| 4,351,466 A | 9/1982 | Noiles |
| 4,379,457 A | 4/1983 | Gravener et al. |
| 4,473,077 A | 9/1984 | NoIles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 4,973,090 A | 11/1990 | Hyduke |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,573,286 A | 11/1996 | Rogozinski |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A | 11/1997 | Seeber |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,233,796 B1 | 5/2001 | van Wassenhove |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |

(56) References Cited

U.S. PATENT DOCUMENTS

| | | |
|---|---|---|
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 | 1/2009 | Roy |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |

(56) References Cited

U.S. PATENT DOCUMENTS

| | | | |
|---|---|---|---|
| 7,938,307 B2 | 5/2011 | Bettuchi | |
| 7,942,302 B2 | 5/2011 | Roby et al. | |
| 7,951,166 B2 | 5/2011 | Orban, III et al. | |
| 7,959,050 B2 | 6/2011 | Smith et al. | |
| 7,967,181 B2 | 6/2011 | Viola et al. | |
| 7,975,895 B2 | 7/2011 | Milliman | |
| 8,002,795 B2 | 8/2011 | Beetel | |
| 8,006,701 B2 | 8/2011 | Bilotti et al. | |
| 8,006,889 B2 | 8/2011 | Adams et al. | |
| 8,011,551 B2 | 9/2011 | Marczyk et al. | |
| 8,011,554 B2 | 9/2011 | Milliman | |
| 8,016,177 B2 | 9/2011 | Bettuchi et al. | |
| 8,016,858 B2 | 9/2011 | Whitman | |
| 8,020,741 B2 | 9/2011 | Cole et al. | |
| 8,025,199 B2 | 9/2011 | Whitman et al. | |
| 8,028,885 B2 | 10/2011 | Smith et al. | |
| 8,038,046 B2 | 10/2011 | Smith et al. | |
| 8,043,207 B2 | 10/2011 | Adams | |
| 8,066,167 B2 | 11/2011 | Measamer et al. | |
| 8,066,169 B2 | 11/2011 | Viola | |
| 8,070,035 B2 | 12/2011 | Holsten et al. | |
| 8,070,037 B2 | 12/2011 | Csiky | |
| 8,096,458 B2 | 1/2012 | Hessler | |
| 8,109,426 B2 * | 2/2012 | Milliman | A61B 17/1114 227/175.1 |
| 8,109,427 B2 | 2/2012 | Orban, III | |
| 8,113,406 B2 | 2/2012 | Holsten et al. | |
| 8,113,407 B2 | 2/2012 | Holsten et al. | |
| 8,118,836 B2 | 2/2012 | Denham | |
| 8,123,103 B2 | 2/2012 | Milliman | |
| 8,128,645 B2 | 3/2012 | Sonnenschein et al. | |
| 8,132,703 B2 | 3/2012 | Milliman et al. | |
| 8,136,712 B2 | 3/2012 | Zingman | |
| 8,146,790 B2 | 4/2012 | Milliman | |
| 8,146,791 B2 | 4/2012 | Bettuchi et al. | |
| 8,172,860 B2 | 5/2012 | Zung et al. | |
| 8,181,838 B2 | 5/2012 | Milliman et al. | |
| 8,192,460 B2 | 6/2012 | Orban, III et al. | |
| 8,201,720 B2 | 6/2012 | Hessler | |
| 8,203,782 B2 | 6/2012 | Brueck et al. | |
| 8,211,130 B2 | 7/2012 | Viola | |
| 8,225,799 B2 | 7/2012 | Bettuchi | |
| 8,225,981 B2 | 7/2012 | Criscuolo et al. | |
| 8,231,041 B2 | 7/2012 | Marczyk et al. | |
| 8,231,042 B2 | 7/2012 | Hessler et al. | |
| 8,257,391 B2 | 9/2012 | Orban, III et al. | |
| 8,267,301 B2 | 9/2012 | Milliman et al. | |
| 8,272,552 B2 | 9/2012 | Holsten et al. | |
| 8,276,802 B2 | 10/2012 | Kostrzewski | |
| 8,281,975 B2 | 10/2012 | Criscuolo et al. | |
| 8,286,845 B2 | 10/2012 | Perry et al. | |
| 8,308,045 B2 | 11/2012 | Bettuchi et al. | |
| 8,312,885 B2 | 11/2012 | Bettuchi et al. | |
| 8,313,014 B2 | 11/2012 | Bettuchi | |
| 8,317,073 B2 | 11/2012 | Milliman et al. | |
| 8,317,074 B2 | 11/2012 | Ortiz et al. | |
| 8,322,590 B2 | 12/2012 | Patel et al. | |
| 8,328,060 B2 | 12/2012 | Jankowski et al. | |
| 8,328,062 B2 | 12/2012 | Viola | |
| 8,328,063 B2 | 12/2012 | Milliman et al. | |
| 8,343,185 B2 | 1/2013 | Milliman et al. | |
| 8,353,438 B2 | 1/2013 | Baxter, III et al. | |
| 8,353,439 B2 | 1/2013 | Baxter, III et al. | |
| 8,353,930 B2 | 1/2013 | Heinrich et al. | |
| 8,360,295 B2 | 1/2013 | Milliman et al. | |
| 8,365,974 B2 | 2/2013 | Milliman | |
| 8,403,942 B2 | 3/2013 | Milliman et al. | |
| 8,408,441 B2 | 4/2013 | Wenchell et al. | |
| 8,413,870 B2 | 4/2013 | Pastorelli et al. | |
| 8,413,872 B2 | 4/2013 | Patel | |
| 8,418,905 B2 | 4/2013 | Milliman | |
| 8,418,909 B2 | 4/2013 | Kostrzewski | |
| 8,424,535 B2 | 4/2013 | Hessler et al. | |
| 8,424,741 B2 | 4/2013 | McGuckin, Jr. et al. | |
| 8,430,291 B2 | 4/2013 | Heinrich et al. | |
| 8,430,292 B2 | 4/2013 | Patel et al. | |
| 8,453,910 B2 | 6/2013 | Bettuchi et al. | |
| 8,453,911 B2 | 6/2013 | Milliman et al. | |
| 8,485,414 B2 | 7/2013 | Criscuolo et al. | |
| 8,490,853 B2 | 7/2013 | Criscuolo et al. | |
| 8,511,533 B2 | 8/2013 | Viola et al. | |
| 8,551,138 B2 | 10/2013 | Orban, III et al. | |
| 8,567,655 B2 | 10/2013 | Nalagatla et al. | |
| 8,579,178 B2 | 11/2013 | Holsten et al. | |
| 8,590,763 B2 | 11/2013 | Milliman | |
| 8,590,764 B2 | 11/2013 | Hartwick et al. | |
| 8,608,047 B2 | 12/2013 | Holsten et al. | |
| 8,616,428 B2 | 12/2013 | Milliman et al. | |
| 8,616,429 B2 | 12/2013 | Viola | |
| 8,622,275 B2 | 1/2014 | Baxter, III et al. | |
| 8,631,993 B2 | 1/2014 | Kostrzewski | |
| 8,636,187 B2 | 1/2014 | Hueil et al. | |
| 8,640,940 B2 | 2/2014 | Ohdaira | |
| 8,662,370 B2 | 3/2014 | Takei | |
| 8,663,258 B2 | 3/2014 | Bettuchi et al. | |
| 8,672,931 B2 | 3/2014 | Goldboss et al. | |
| 8,678,264 B2 | 3/2014 | Racenet et al. | |
| 8,684,248 B2 | 4/2014 | Milliman | |
| 8,684,251 B2 | 4/2014 | Rebuffat et al. | |
| 8,684,252 B2 | 4/2014 | Patel et al. | |
| 8,733,611 B2 | 5/2014 | Milliman | |
| 9,033,374 B1 | 5/2015 | Sadeck | |
| 9,517,070 B2 * | 12/2016 | Mulreed | A61B 17/0469 |
| 9,668,740 B2 * | 6/2017 | Williams | A61B 17/07207 |
| 9,861,367 B2 | 1/2018 | Williams | |
| 10,470,772 B2 | 11/2019 | Williams | |
| 2003/0101944 A1 | 6/2003 | Heinrichs | |
| 2003/0111507 A1 | 6/2003 | Nunez | |
| 2003/0178852 A1 | 9/2003 | McNicholas | |
| 2004/0251688 A1 | 12/2004 | Safwat | |
| 2005/0051597 A1 | 3/2005 | Toledano | |
| 2005/0107813 A1 | 5/2005 | Gilete Garcia | |
| 2006/0000869 A1 | 1/2006 | Fontayne | |
| 2006/0011698 A1 | 1/2006 | Okada et al. | |
| 2006/0201989 A1 | 9/2006 | Ojeda | |
| 2006/0208016 A1 | 9/2006 | Esch | |
| 2007/0027473 A1 | 2/2007 | Vresh et al. | |
| 2007/0029363 A1 | 2/2007 | Popov | |
| 2007/0060952 A1 | 3/2007 | Roby et al. | |
| 2008/0228223 A1 | 9/2008 | Alkhatib | |
| 2009/0082785 A1 * | 3/2009 | Milliman | A61B 17/1155 606/139 |
| 2009/0236392 A1 | 9/2009 | Cole et al. | |
| 2009/0236398 A1 | 9/2009 | Cole et al. | |
| 2009/0236401 A1 | 9/2009 | Cole et al. | |
| 2010/0019016 A1 | 1/2010 | Edoga et al. | |
| 2010/0038401 A1 * | 2/2010 | Milliman | A61B 17/068 227/175.1 |
| 2010/0051668 A1 | 3/2010 | Milliman et al. | |
| 2010/0084453 A1 | 4/2010 | Hu | |
| 2010/0147923 A1 | 6/2010 | D'Agostino et al. | |
| 2010/0163598 A1 | 7/2010 | Belzer | |
| 2010/0170932 A1 * | 7/2010 | Wenchell | A61B 17/1155 227/176.1 |
| 2010/0224668 A1 | 9/2010 | Fontayne et al. | |
| 2010/0230465 A1 | 9/2010 | Smith et al. | |
| 2010/0258611 A1 | 10/2010 | Smith et al. | |
| 2010/0264195 A1 | 10/2010 | Bettuchi | |
| 2010/0327041 A1 | 12/2010 | Milliman et al. | |
| 2011/0011916 A1 | 1/2011 | Levine | |
| 2011/0114697 A1 | 5/2011 | Baxter, III et al. | |
| 2011/0114700 A1 | 5/2011 | Baxter, III et al. | |
| 2011/0144640 A1 | 6/2011 | Heinrich et al. | |
| 2011/0147432 A1 | 6/2011 | Heinrich et al. | |
| 2011/0192882 A1 | 8/2011 | Hess et al. | |
| 2012/0145755 A1 | 6/2012 | Kahn | |
| 2012/0193395 A1 | 8/2012 | Pastorelli et al. | |
| 2012/0193398 A1 | 8/2012 | Williams et al. | |
| 2012/0232339 A1 | 9/2012 | Csiky | |
| 2012/0273548 A1 | 11/2012 | Ma et al. | |
| 2012/0325888 A1 | 12/2012 | Qiao et al. | |
| 2013/0015232 A1 | 1/2013 | Smith et al. | |
| 2013/0020372 A1 | 1/2013 | Jankowski et al. | |
| 2013/0020373 A1 | 1/2013 | Smith et al. | |

(56) References Cited

U.S. PATENT DOCUMENTS

| | | |
|---|---|---|
| 2013/0032628 A1 | 2/2013 | Li et al. |
| 2013/0037599 A1 | 2/2013 | Rebuffat et al. |
| 2013/0056516 A1 | 3/2013 | Viola |
| 2013/0060258 A1 | 3/2013 | Giacomantonio |
| 2013/0105546 A1 | 5/2013 | Milliman et al. |
| 2013/0105551 A1 | 5/2013 | Zingman |
| 2013/0126580 A1 | 5/2013 | Smith et al. |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2014/0151430 A1 | 6/2014 | Scheib et al. |

FOREIGN PATENT DOCUMENTS

| | | |
|---|---|---|
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 2415407 A1 | 2/2012 |
| EP | 2524656 A2 | 11/2012 |
| EP | 2873380 A1 | 5/2015 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 0154594 A1 | 8/2001 |
| WO | 2008107918 A1 | 9/2008 |

OTHER PUBLICATIONS

Extended European Search Report issued in corresponding EP 15173264 dated Feb. 29, 2016.

Australian Office Action dated Feb. 12, 2019, issued in AU Appln. No. 2015202336.

Japanese Office Action dated Feb. 27, 2019, issued in JP Appln. No. 2015111387.

* cited by examiner

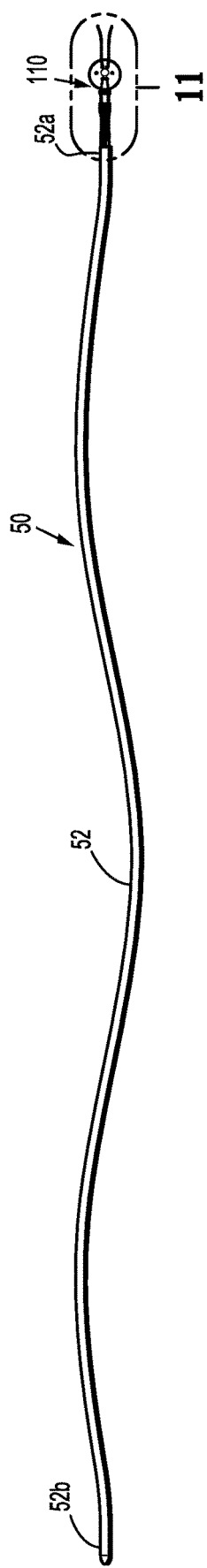
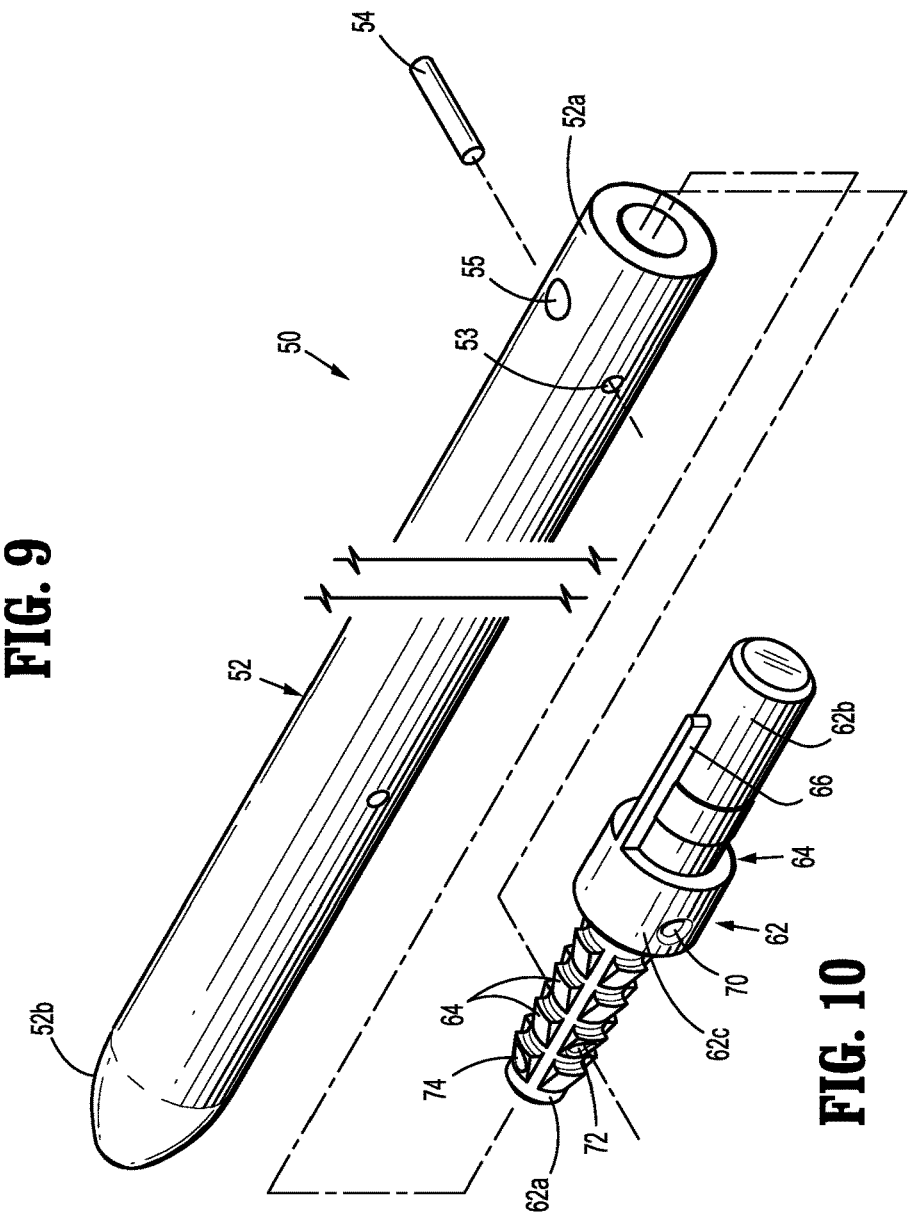
FIG. 9
FIG. 10

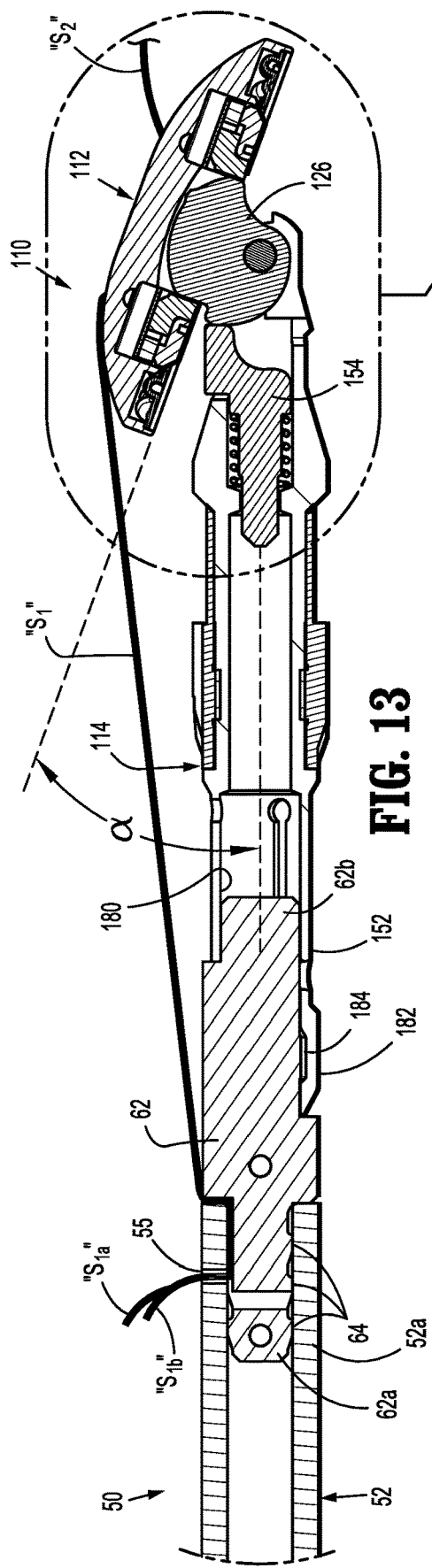
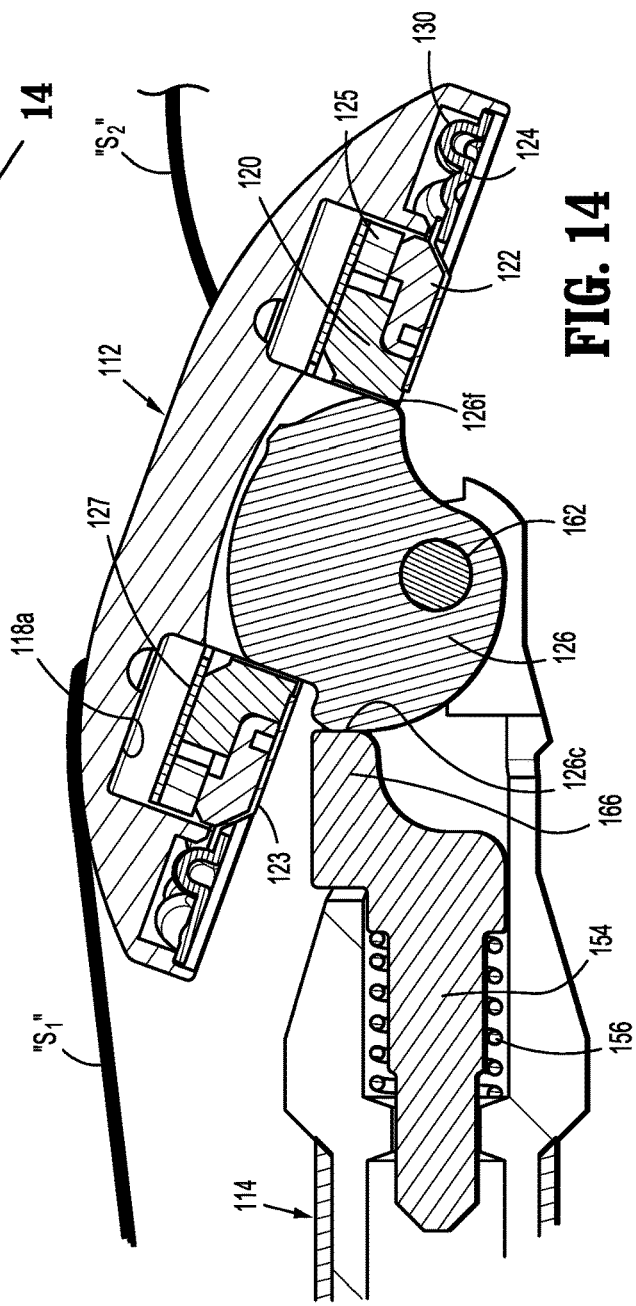

ANVIL ASSEMBLY DELIVERY SYSTEMS

CROSS-REFERENCE TO RELATED APPLICATIONS

This application is a continuation of U.S. patent application Ser. No. 15/831,679, filed Dec. 5, 2017, which is a divisional of U.S. patent application Ser. No. 14/313,303, filed Jun. 24, 2014. Each of these applications is hereby incorporated herein by reference in its entirety.

BACKGROUND

Technical Field

The present disclosure relates to an anvil assembly for use with a surgical stapling device. More particularly, the present disclosure relates to a delivery system for trans-oral delivery of the anvil assembly.

Background of Related Art

Trans-oral delivery systems for delivering an anvil assembly to a surgical site, e.g., the stomach, are known. In known delivery systems, a guide suture is threaded through one or more openings in the head of the anvil assembly to facilitate trans-oral insertion of the anvil assembly. The guide suture which include ends that remain external of the patient's mouth, may be used by the surgeon to dislodge the anvil assembly if it becomes stuck during trans-oral delivery and/or to retrieve the anvil assembly in the event of a patient emergency, e.g., cardiac arrest. Improved methods for securing the guide suture to an anvil assembly to facilitate detachment of the guide suture from the anvil assembly once the anvil assembly is delivered to the surgical site and/or the stapling procedure has been performed would be desirable.

SUMMARY

An anvil delivery system is provided. The system includes a delivery assembly and an anvil assembly selectively securable to the delivery assembly. The anvil assembly includes a center rod assembly and a head assembly pivotally secured to the anvil center rod about a pivot axis and movable between a first tilted position, an operative position, and a second tilted position. The head assembly including a housing, a cutting ring, and an anvil plate, the housing defining a throughbore passing through the housing and between the cutting ring and the anvil plate. The anvil delivery system further includes a retaining suture selectively secured between the head assembly and the delivery assembly for retaining the head assembly in the first tilted position and a retrieval suture received through the throughbore of the housing and having at least one end extending distally from the anvil assembly.

In some embodiments, the retrieval suture extends the length of the center rod assembly. The delivery member may include a flexible tube and an adapter member. The retrieval suture may be frictionally secured between the flexible tube and the adapter member. The retrieval suture may include a loop and the retaining suture being received through the loop. Alternatively, the retrieval suture is received about the center rod assembly. The retrieval suture may extend across the cutting ring when the head assembly is in the operative position.

Also provided is a method of securing a guide suture to an anvil assembly. The method includes providing an anvil assembly including a center rod assembly and a head assembly, the head assembly defining at least one throughbore, receiving a first end of a retrieval suture through the at least one throughbore, forming a loop in the retrieval suture, and receiving the first end of the retrieval suture through the at least one throughbore. The method may further include attaching an anvil delivery system to a distal end of the center rod assembly and securing the loop in the retrieval suture to the anvil delivery system. Forming the loop in the retrieval suture may include wrapping the first end of the suture around a retaining suture. Forming the loop in the retrieval suture may instead include wrapping the first end of the suture around the center rod assembly. The method may further include receiving the loop in the retrieval suture about the center rod assembly.

Another method of securing a guide suture to an anvil assembly is provided. The method includes providing an anvil assembly including a center rod assembly and a head assembly pivotally secured to the center rod assembly, the head assembly defining a throughbore, receiving a loop of a retrieval suture through the throughbore in the head assembly of the anvil assembly, and securing the loop relative to the head assembly. Securing the loop relative to the head assembly may include attaching an anvil delivery system to the center rod assembly and securing the loop of the retrieval suture between the center rod assembly and the delivery system. Securing the loop relative to the head assembly may instead include selectively securing a retaining suture to the head assembly and receiving the retaining suture through the loop in the retrieval suture. Alternatively, securing the loop relative to the head assembly includes receiving the loop of the retrieval suture about the center rod assembly.

BRIEF DESCRIPTION OF THE DRAWINGS

Various embodiments of the presently disclosed anvil assembly and anvil assembly delivery system are disclosed herein with reference to the drawings wherein:

FIG. 9 is a top view of the anvil assembly of FIGS. 1-7 supported on an anvil delivery system;

FIG. 10 is an enlarged exploded view of the anvil delivery system of FIG. 9;

FIG. 13 is a cross sectional side view of the anvil assembly of FIGS. 1-7, in a pre-fired tilted position supported on the anvil delivery system of FIGS. 9-12;

FIG. 14 is an enlarged view of the indicated area of detail shown in FIG. 13;

DETAILED DESCRIPTION OF EMBODIMENTS

Figure 1:
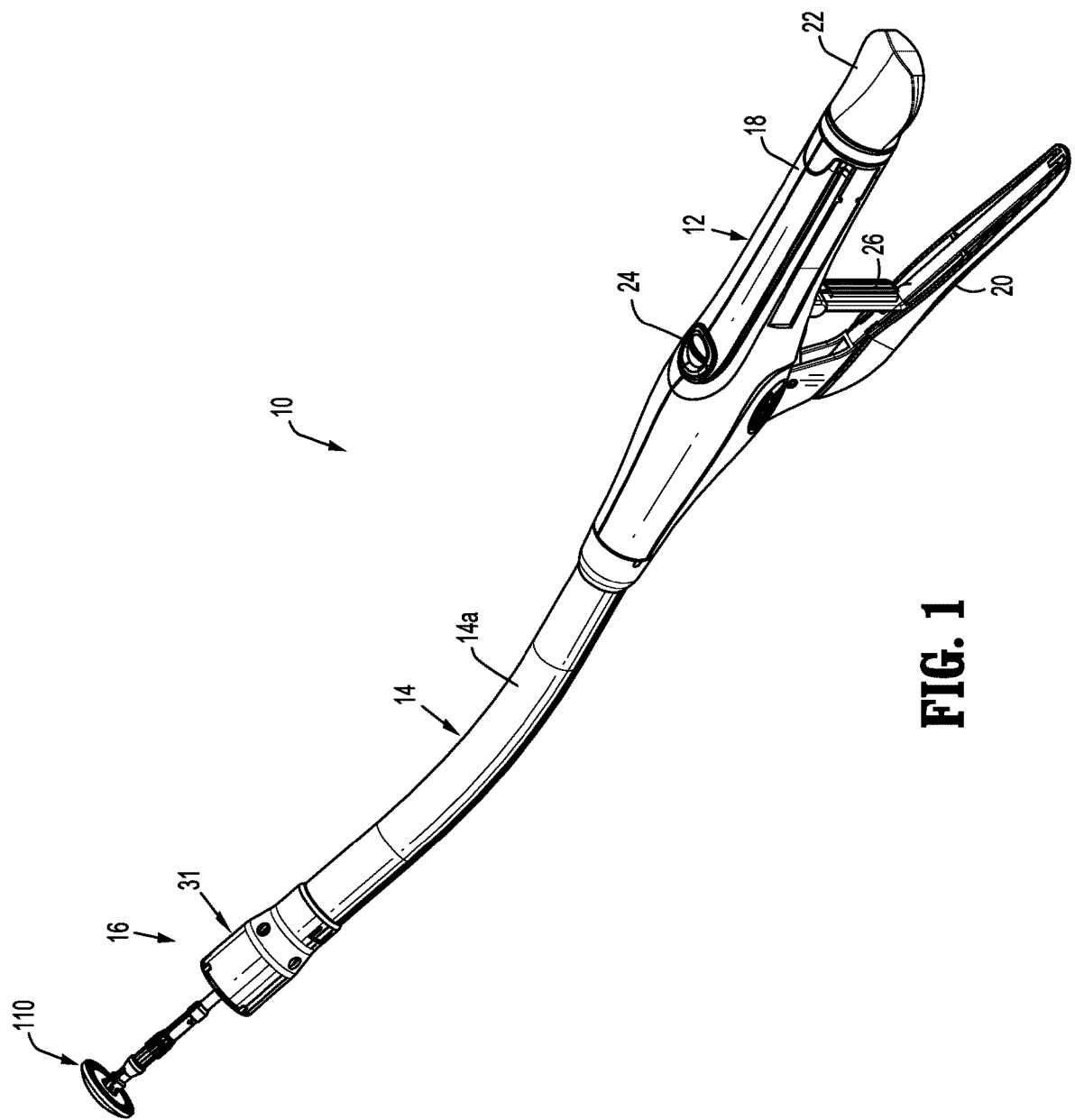
FIG. 1 is a perspective view of a surgical stapling device including an embodiment of an anvil assembly according to the present disclosure.
Figure 2:
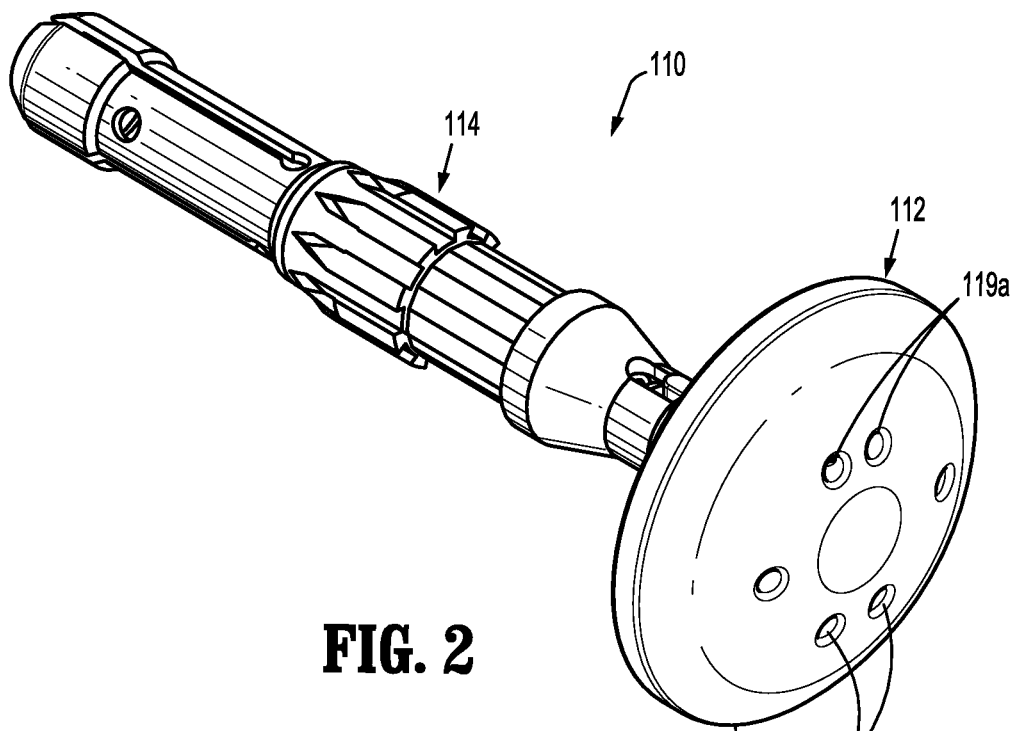
FIG. 2 is a first perspective side view of the anvil assembly of FIG. 1.

Embodiments of the presently disclosed anvil assembly delivery system will now be described in detail with reference to the drawings in which like reference numerals designate identical or corresponding elements in each of the several views. Throughout this description, the term "proximal" will refer to the portion of the instrument closest to the operator and the term "distal" will refer to the portion of the instrument furthest from the operator.

FIG. 1 illustrates an embodiment of a surgical stapling device configured for use with tilt anvil assemblies according to the present disclosure. Briefly, surgical stapling device 10 includes a proximal handle assembly 12, an elongated central body portion 14 including a curved elongated outer tube 14a, and a distal head portion 16. Alternately, in some surgical procedures, e.g., the treatment of hemorrhoids, it is desirable to have a substantially straight, shortened, central body portion. The length, shape and/or the diameter of body portion 14 and distal head portion 16 may also be varied to suit a particular surgical procedure.

With reference still to FIG. 1, handle assembly 12 includes a stationary handle 18, a firing trigger 20, a rotatable approximation knob 22 and an indicator 24. A pivotally mounted trigger lock 26 is fastened to handle assembly 12 and is manually positioned to prevent inadvertent firing of stapling device 10. Indicator 24 is positioned on the stationary handle 18 and includes indicia, e.g., color coding, alpha-numeric labeling, etc., to identify to a surgeon whether the device is approximated and is ready to be fired. Head portion 16 includes an anvil assembly 110 and a shell assembly 31. For a more detailed discussion of surgical stapler 10, please refer to commonly owned U.S. Pat. No. 7,364,060 to Milliman, the contents of which is incorporated herein by reference in its entirety.

Referring now to FIGS. 2-7, an anvil assembly according to an embodiment of the present disclosure is shown generally as anvil assembly 110. Anvil assembly 110 is shown in a non-titled position or operative position. Anvil assembly 110 includes a head assembly 112 and a center rod assembly 114. Head assembly 112 includes a post 116, a housing 118, a backup member or plate 120, a cutting ring 122, a cutting ring cover 123, an anvil plate 124, a spacer or washer 125, a cam latch member 126, and a retainer member 127. Post 116 is monolithically formed with and centrally positioned within housing 118. Alternately, housing 118 and post 116 may be formed separately and fastened together using a known fastening technique, e.g., welding.

As will be discussed in further detail below, housing 118 includes openings 119a, 119b sized and dimensioned to receive one or more sutures "S". During use, a first suture "$S_1$" (FIG. 9) is inserted through openings 119a and is used to retain head assembly 112 in a retracted or first tilted position (FIG. 9) during insertion of anvil assembly 110 within a patient. A second suture "$S_2$" (FIG. 9) is inserted through openings 119b. The second suture "$S_2$" is configured to facilitate guiding tilt anvil assembly 110 trans-orally within a patient. During trans-oral insertion of anvil assembly 110, suture "$S_2$" extends from the mouth of patient, permitting the anvil assembly 110 to be retrieved trans-orally.

With reference still to FIGS. 2-7, anvil plate 124 is supported in an outer annular recess 128 of housing 118 and includes a plurality of staple deforming pockets 130 for receiving and deforming staples. At least one tab 124a extends radially outwardly from anvil plate 124 and is received within a cutout 132 formed in an outer rim of housing 118. Tab 124a and cutout 132 function to align or properly position anvil plate 124 within annular recess 128 of housing 118.

Figure 7:
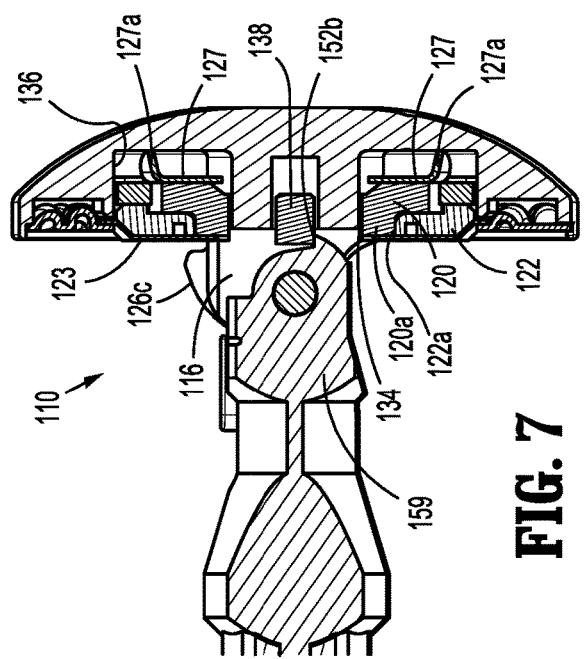
FIG. 7 is a cross-sectional side view of a distal end of the anvil assembly of FIGS. 1-6 taken along line 7-7 of FIG. 5.
Figure 6:
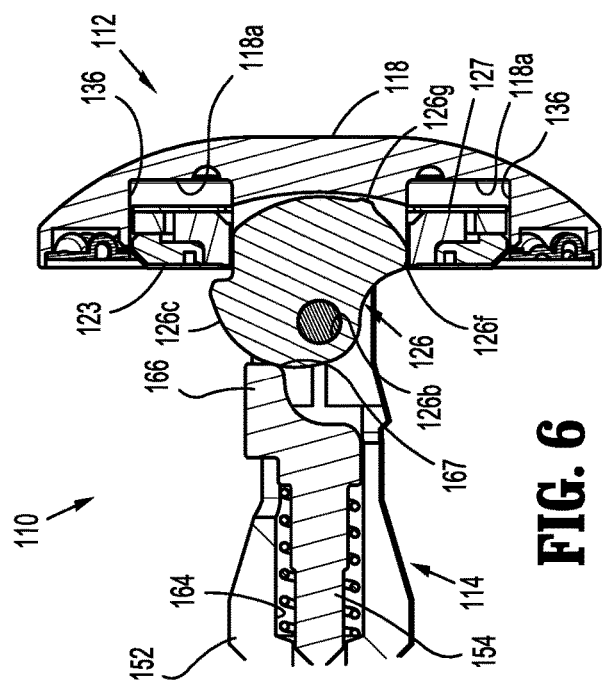
FIG. 6 is a cross-sectional side view of a distal end of the tilt anvil assembly of FIGS. 1-6 taken along line 6-6 of FIG. 5.
Figure 5:
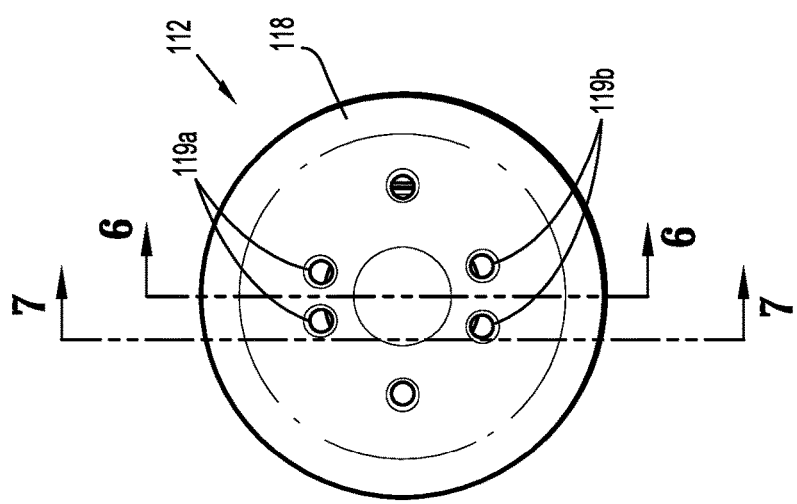
FIG. 5 is an end view of the anvil assembly of FIGS. 1-4.

With particular reference to FIGS. 6 and 7, head assembly 112 will be described in detail. Backup plate 120 includes a central opening 134 which is positioned about post 116 within an inner annular recess 136 of housing 118 between post 116 and outer annular recess 128. Backup plate 120 includes a raised platform 120a. Cutting ring 122 includes an opening 122a having a configuration substantially the same as platform 120a. Although platform 120a is illustrated as having a circular shape, other configurations are envisioned, e.g., square, rectangular, triangular, etc. In one embodiment, cutting ring 122 is formed from polyethylene and is fixedly secured to backup plate 120 using, for example, an adhesive, to form a backup plate/cutting ring assembly. Backup plate 120 is formed from a hard material, e.g., a metal. Alternately other materials of construction may be used to construct backup plate 120 and cutting ring 122. Further, backup plate 120 and cutting ring 122, in the alternative, can be formed as a single or unitary structure.

Still referring to FIGS. 6 and 7, a cutting ring cover 123 is secured to an outwardly facing or proximal surface of cutting ring 122 using, for example, an adhesive. In one embodiment, cutting ring cover 123 is formed from a material or materials, which have a hardness greater than that of the cutting ring, e.g., mylar. In one embodiment, cutting ring cover 123 includes two layers of mylar (not shown) which are joined together using an adhesive and a polypropylene coating. Alternately, cutting ring 122 need not have a cover. Cutting ring 122 and backup plate 120 are slidably mounted about post 116. Backup plate 120 includes a pair of inwardly extending fingers 138 which will be described in further detail below.

With reference still to FIGS. 6 and 7, retainer member 127 is positioned in inner annular recess 136 between backup plate 120 and a back wall 118a of housing 118. In one embodiment, retainer member 127 is annular and includes a plurality of deformable tabs 127a which engage a rear surface of backup plate 120. Retainer member 127 prevents backup plate 120 and cutting ring 122 from moving or being pushed into inner annular recess 136 of housing 118 until a predetermined force sufficient to deform tabs 127a has been applied to the backup plate/cutting ring assembly. The predetermined force can be close to but is less than the force applied by an annular cutting blade of a surgical stapling device when it engages, for example, the cutting ring of anvil assembly 110. In one embodiment by way of example, the predetermined force is between about ten pounds and about ninety pounds and can be about thirty (30) pounds. When the predetermined force is reached, e.g., during cutting of tissue, backup plate 120 is urged into inner annular recess 136 and compresses retainer member 127. It is envisioned that other crushable, deformable, collapsible or movement restricting members may be used to retain the backup plate/cutting ring assembly in a fixed position until a predetermined force has been applied to the backup plate/cutting ring assembly.

Turning back to FIG. 4, anvil center rod assembly 114 includes a center rod 152, a plunger 154 and plunger spring 156. A first end of center rod 152 includes a pair of arms 159 which define a cavity 159a. Each arm 159 has a transverse throughbore 158 which is aligned with a central longitudinal axis of center rod 152. Alternately, throughbores 158 can be offset from the longitudinal axis of center rod 152. Post 116 of anvil head assembly 112 is dimensioned to be positioned within cavity 159a and also includes a transverse throughbore (not shown). A pivot member 162 pivotally secures post 116 to center rod 152 via the through bores such that anvil head assembly 112 may be pivotally mounted to anvil center rod assembly 114.

Figure 3:
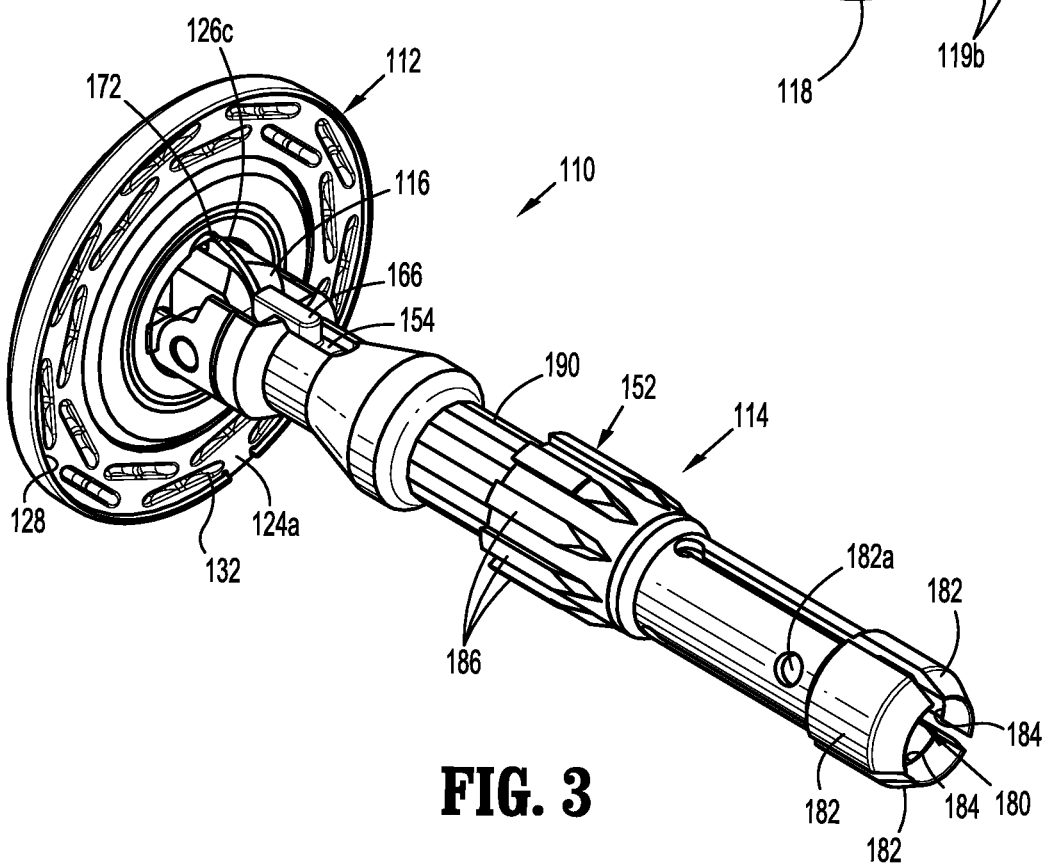
FIG. 3 is a second perspective side view of the anvil assembly shown in FIGS. 1 and 2.
Figure 8:
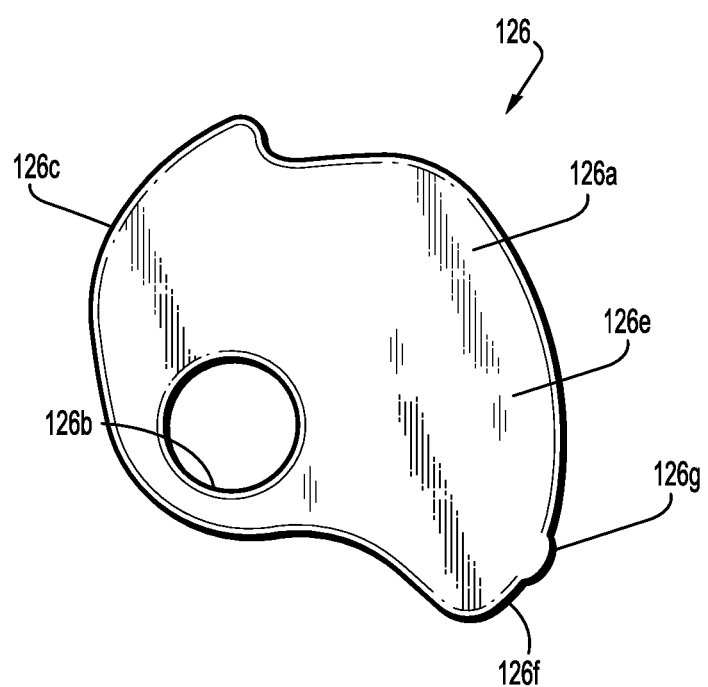
FIG. 8 is an enlarged side view of the cam latch member of the anvil assembly of FIGS. 1-7.
Figure 11:
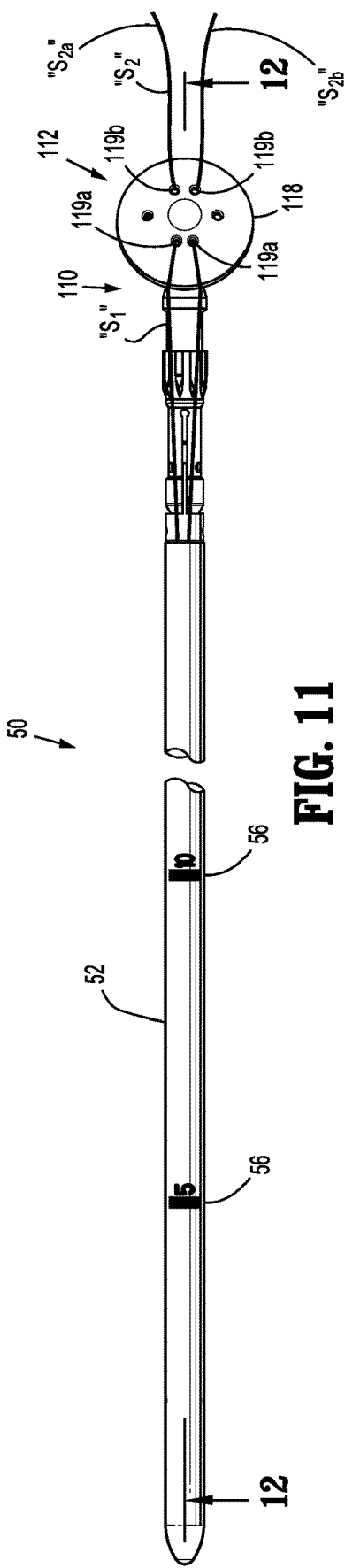
FIG. 11 an enlarged top view of the anvil delivery system of FIGS. 9 and 10, including the anvil assembly of FIGS. 1-7.
Figure 12:
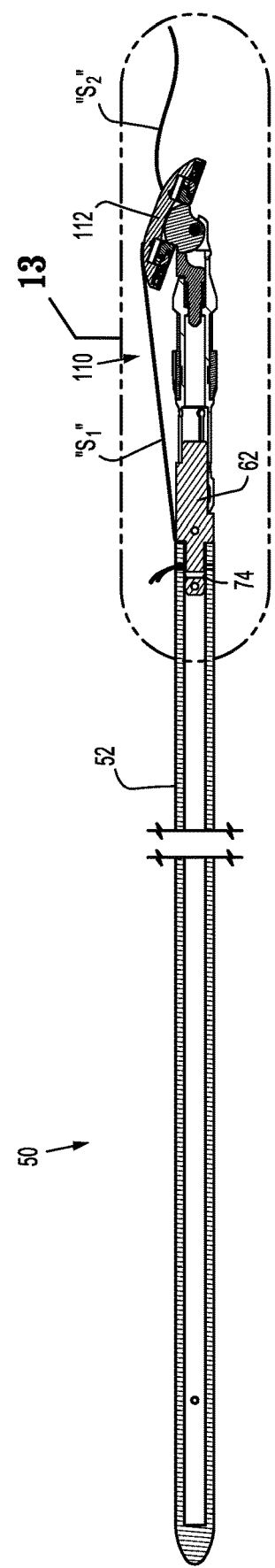
FIG. 12 is a cross-sectional side view of the anvil assembly and anvil assembly delivery system of FIG. 11 taken along lines 12-12 of FIG. 11.

Turning briefly to FIG. 8, cam latch member 126 includes a body 126a having a throughbore 126b. Throughbore 126b is dimensioned to receive pivot member 162 such that cam latch member 126 is pivotally mounted within transverse slot 172 (FIG. 3) of post 116 about pivot member 162. Referring now to FIGS. 3, 6 and 7, cam latch member 126 includes a first body portion 126c which extends partially from slot 172 of post 116 and is positioned to be engaged by a finger 166 of plunger 154. First body portion 126c is configured such that the distance between the surface of first body portion 126c and through bore 126b increase in a clockwise direction about cam latch member 126. In this manner, plunger 154 is able to move forward as cam latch member 126 rotates in a clockwise direction. Additionally, this configuration of first body portion 126c permits plunger 154 to be retracted as cam latch member rotates in a counter-clockwise direction. Cam latch member 126 also includes an edge 126f, including a tab 126 b. A leading portion of edge 126f is configured to be urged into engagement with an inner periphery 120b of backup plate 120 by an engagement finger 166 of plunger 154 when anvil head 112 is in its non-tilted or operative position. Tab 126g is configured to engage backwall 118a of housing 118 to prevent cam latch member 126 from rotating counter-clockwise relative to housing 118.

With reference to FIG. 6, plunger 154 is slidably positioned in a bore 164 formed in the first end of center rod 152. Plunger 154 includes an engagement finger 166 which is offset from the pivot axis of anvil head assembly 112 and biased into engagement with an edge 126c of cam latch 126. Engagement of finger 166 with edge 126c of cam latch 126 presses a leading portion of edge 126f against an inner periphery of back plate 120 to urge anvil head assembly 112 to an operative or non-tilted position on center rod 152.

Turning to FIG. 7, in the pre-fired operative position of head assembly 112, i.e. when head assembly 112 has been pivoted to its non-tilted position, fingers 138 formed on backup plate 120 engage protrusions 152b adjacent top surface 152a of center rod 152 to prevent head assembly 112 from pivoting about pivot member 162. Anvil head assembly 112 may be tilted a degrees (FIG. 13) relative to anvil center rod assembly 114 in the pre-fired tilted position. In one embodiment, anvil head assembly 112 is tilted about seventy degrees (70°) in its pre-fired tilted position; however it should be understood that tilting head assembly 112 to other degrees is also contemplated. Titling of anvil head assembly 112 relative to anvil center rod assembly 114 causes body portion 126c of cam latch member 126 to engage finger 166 of plunger 154. As cam latch assembly 126 rotates with the tilting of anvil head assembly 112, plunger 154 is retracted with bore 164 of anvil center rod assembly 114, thereby compressing spring 156. In this manner, finger 166 of plunger 154 is distally biased against body portion 126c of cam latch member 126.

Figure 4:
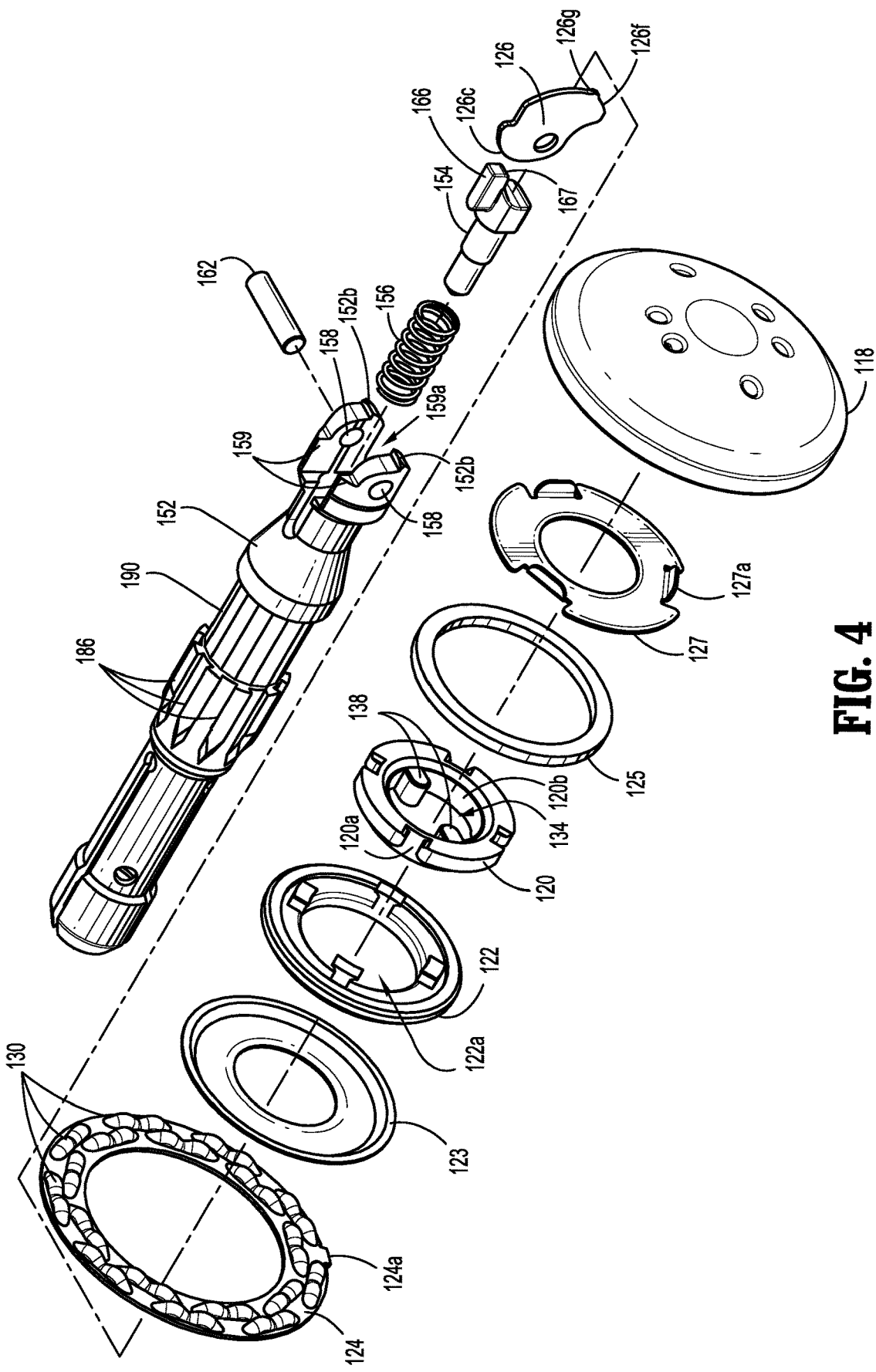
FIG. 4 is an exploded side view of the anvil assembly of FIGS. 1-3.
Figure 18:
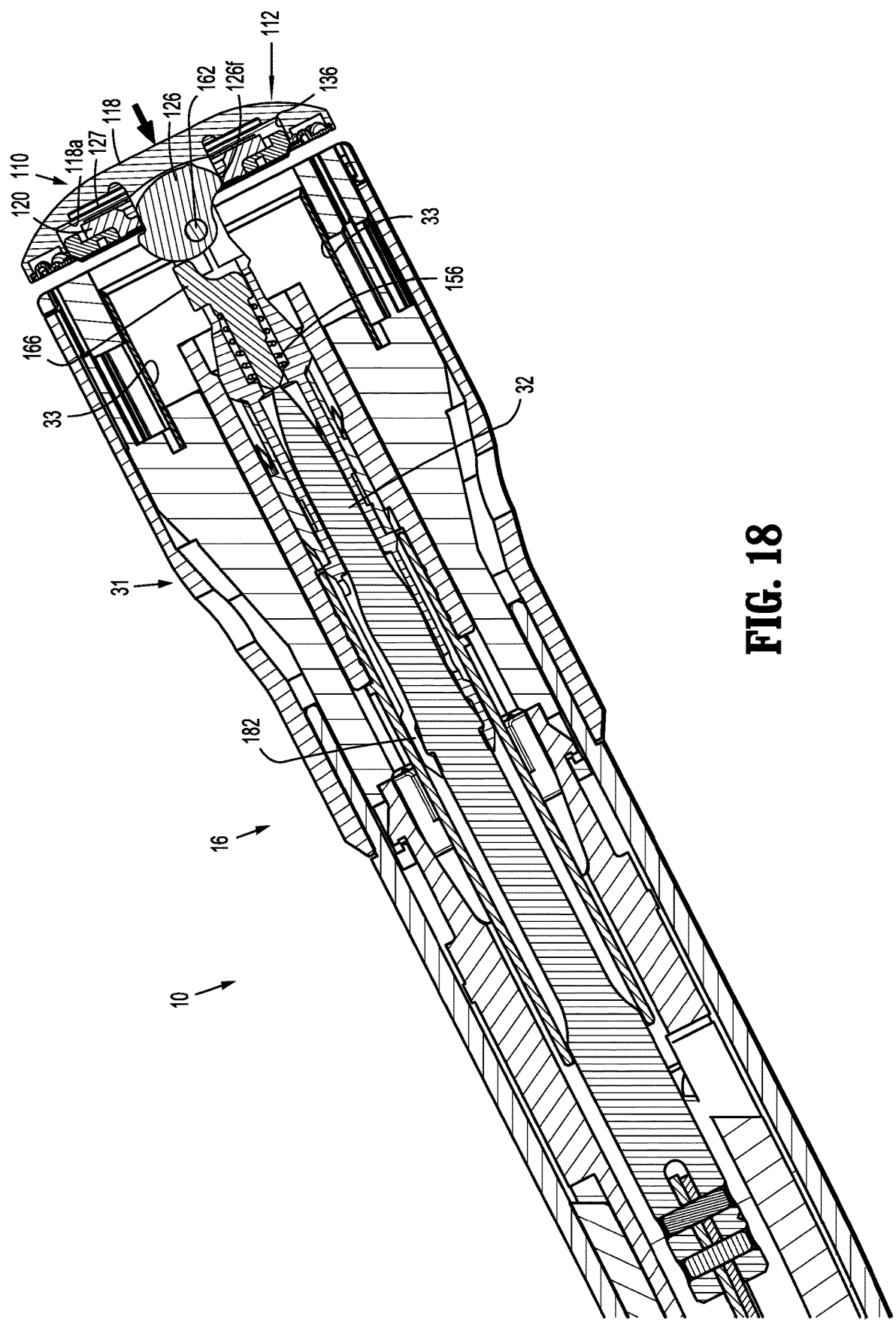
FIG. 18 is an enlarged cross-sectional side view of the distal head portion of the surgical stapling device of FIG. 1 and the anvil assembly of FIGS. 1-7 in a pre-fired non-tilted operative position.
Figure 19:
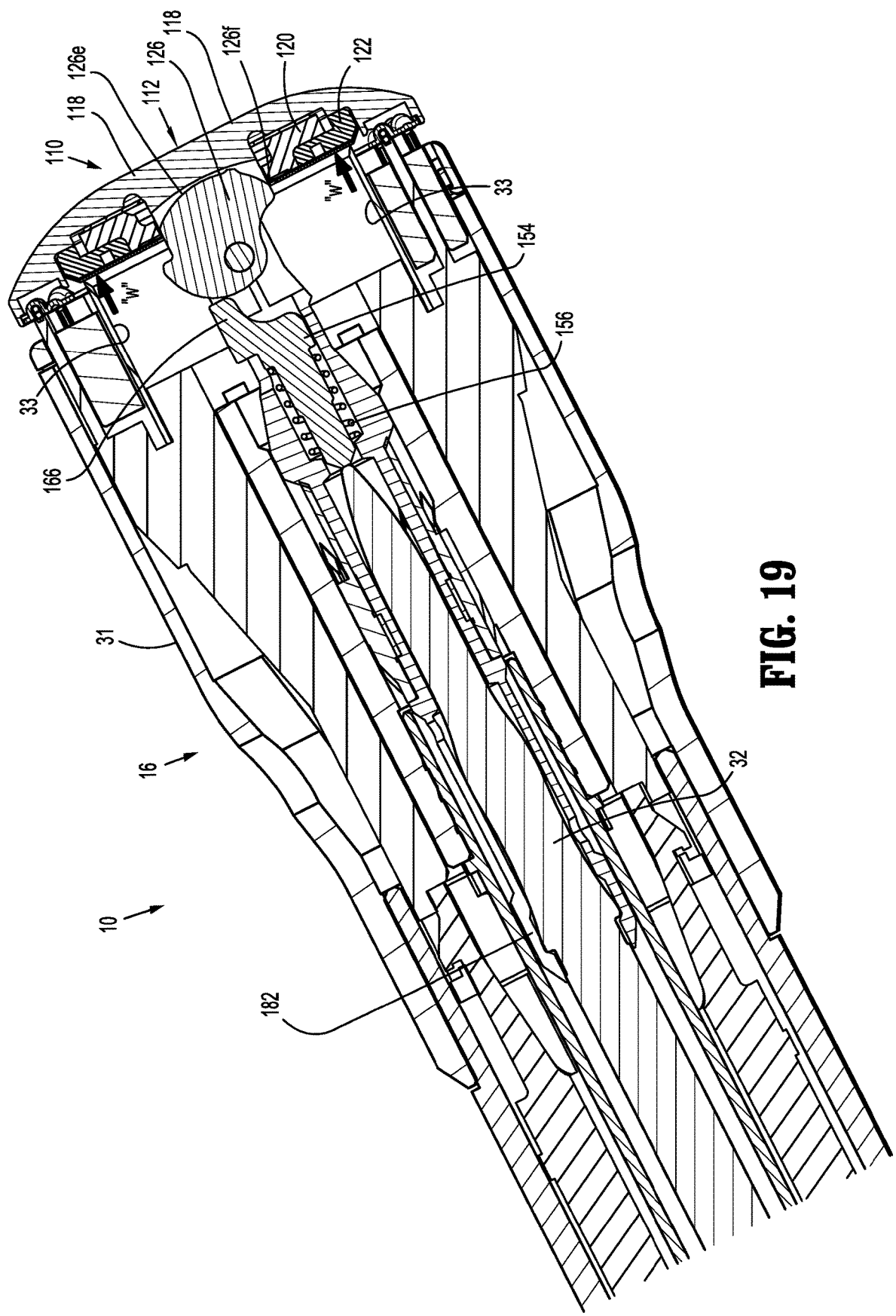
FIG. 19 is an enlarged cross-sectional side view of the distal head portion of the surgical stapling device of FIG. 1 and the anvil assembly of FIGS. 1-7 in a post-fired non-titled operative position.
Figure 20:
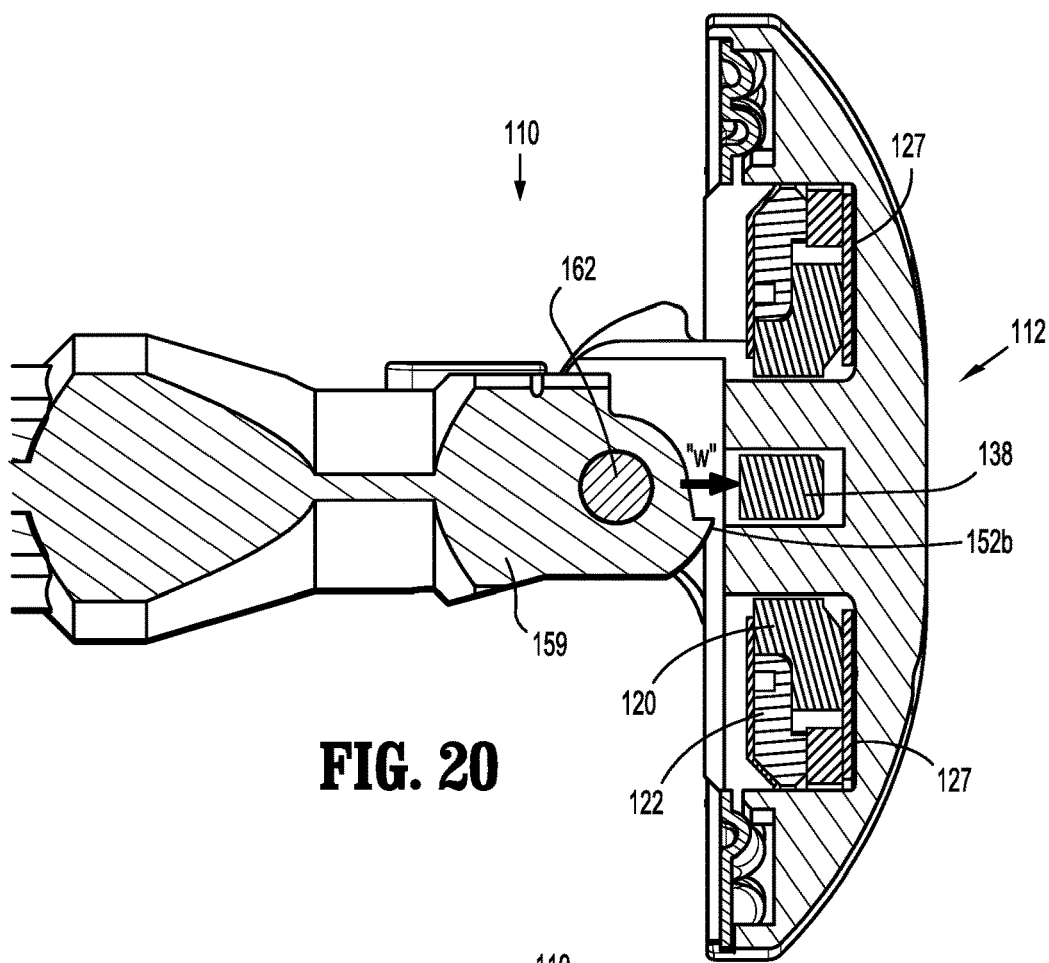
FIG. 20 is an enlarged cross-sectional side view of the distal end of the anvil assembly of FIGS. 1-7 in the post-fired operative position.
Figure 21:
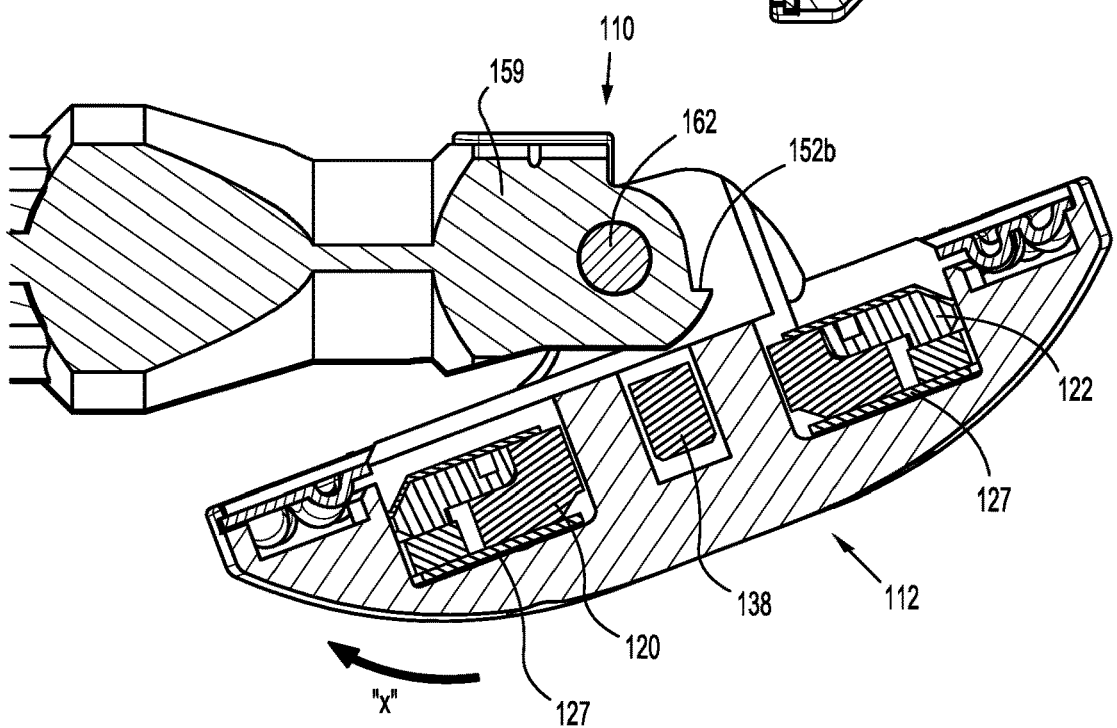
FIG. 21 is an enlarged cross-sectional side view of the distal end of the anvil assembly of FIGS. 1-7 in a post-fired tilted position.

With reference to FIGS. 3 and 4, a second end of center rod 152 includes a bore 180 defined by a plurality of flexible arms 182. Flexible arms 182 each include an opening 182a dimensioned to receive a projection formed on or connected to a shell assembly 31 (FIG. 18). Alternatively, openings 182a may be configured to receive a suture for permitting retrieval of anvil assembly 110. The proximal ends of each of the flexible arms 182 include an internal shoulder 184 dimensioned to releasably engage shell assembly 31 of surgical stapling device 10 to secure anvil assembly 110 to the surgical stapling device. A plurality of splines 186 are formed about center rod 152. Splines 186 function to align anvil assembly 110 with the staple holding portion of a surgical stapling device. Center rod 152 also includes an annular recessed portion 190 to facilitate grasping of anvil assembly 110 by a surgeon with a grasper. Recessed portion 190 may include a roughened or knurled surface or an overmold to facilitate grasping of anvil assembly 110.

With reference now to FIGS. 9-12, a system for delivering anvil assembly 110 within a patient is shown generally as anvil delivery system 50. Anvil delivery system 50 includes a flexible tube 52 and an adapter 62. Flexible tube 52 includes an open end 52a. Adapter 62 and anvil assembly 110 are supported on open end 52a of flexible tube 52. Open end 52a of flexible tube 52 includes a through bore 53 extending therethrough configured to receive a locking pin 54. Open end 52a further includes an opening 55. Closed end 52b of flexible tube 52 is configured for trans-orally receipt in a patient. Flexible tube 52 may include markings or other gradations 56 along the length thereof to indicate to a surgeon how much of flexible tube 52 has been received within the patient during insertion and/or to indicate the length of flexible tube 52 remaining in the patient upon removal.

With particular reference to FIG. 10, adapter 62 includes a first end 62a configured to be received within open end 52a of flexible tube 52 and a second end 62b is configured to be received with in bore 180 formed in center rod 152 of anvil assembly 110. First end 62a includes a series of annular rings 64 configured to frictionally retain first end 62a of adapter 62 within open end 52a of flexible tube 52. Second end 62b of adapter 62 includes a longitudinal guide member 66 configured to be received between flexible arms 182 formed in center rod 152 of anvil assembly 110. In addition, second end 62b of adapter 62 is sized to allow center rod 154 of anvil assembly 110 to freely slide into and off second end 62b of adapter 62. Adapter 62 further includes a first through bore 70 formed in a central hub portion 62c as well as second and third through bores 72, 74 formed in first end 62a. Through bore 72 is configured to align with through bore 53 formed in open end 52a of flexible tube 52 and is sized to receive locking pin 54.

With particular reference now to FIGS. 10, 13 and 14, anvil assembly 110 is supported on anvil delivery system 50. Securing anvil assembly 110 to anvil delivery system 50 requires first that suture "$S_1$" is thread through openings 119a formed on anvil head 112 such that first and second ends of suture "$S_1$" are positioned on opposites of center rod 152. Next, second end 62b of adapter 62 is positioned within through bore 180 of center rod 152 such that longitudinal guide 66 is received between two of arm members 182. Each of the first and second ends of suture "$S_1$" is inserted through opening 55 formed in open end 52a of flexible member 52. Anvil head 112 is then rotated to a first tilted position while first and second ends of suture "$S_1$" are pulled through opening 55. First end 62a of adapter 62 is then inserted into open end 52a of flexible member. The frictional contact between annular rings 64 of first end 62a of adapter 62 and an inner surface of flexible tube 52 secures adapter 62 to flexible tube 52 and prevents suture "$S_1$" from loosening. It is envisioned that more than one suture may be used to secure anvil head assembly 112 in a pre-fired tilted position.

Figure 15:
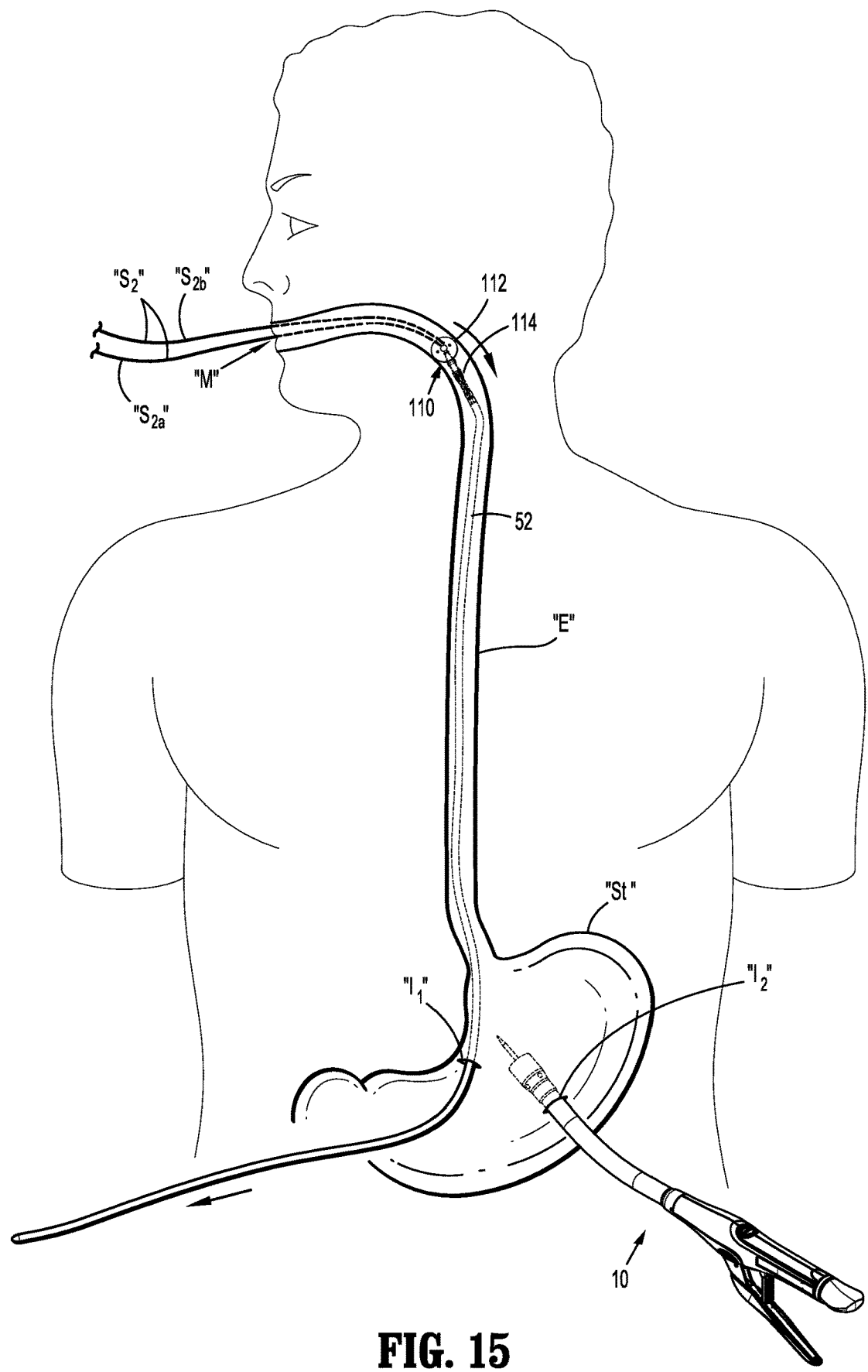
FIG. 15 is an illustration of the anvil assembly and anvil delivery system of FIGS. 11 and 12 being inserted trans-orally into a patient.

With reference now to FIG. 15, a method for delivering anvil assembly 110 to a surgical site within a patient will be described. In one method, anvil assembly 110 is provided in the first tilted position supported on anvil delivery system 50 and ready for delivery. Alternatively, a clinician secures anvil assembly 110 to anvil delivery system 50 as discussed above. Once anvil assembly 110 has been secured to flexible tube 52, the surgeon inserts closed end 52b of flexible tube 52 in the patient's mouth "M" and moves closed end 52b along with flexible tube 52 down through esophagus "E" to a surgical site, i.e., the stomach "St".

After insertion, the surgeon then makes a first incision "$I_1$" at the surgical site (stomach "St" as shown) to create an inner access to closed end 52b of flexible tube 52 and then pulls open end 52b of flexible tube 52 through first incision "$I_1$". In some procedures it may be beneficial to pull flexible tube 52 through incision "$I_1$" until center rod 152 of anvil assembly 110 advances through first incision "$I_1$". When anvil assembly 110 is properly positioned at the surgical site, the surgeon releases anvil delivery system 50 from anvil assembly 110 by cutting suture "$S_1$" and separating anvil assembly 110 from second end 62b of adapter 62. Flexible tube 52 (with fitting 62) may then be pulled from the body through first incision "$I_1$".

Severing of suture "$S_1$" permits plunger 154 to extend from within bore 164, thereby causing finger 166 to engage body portion 126c of cam latch member 126. Rotation of cam latch member 126 causes edge 126f of latch member 126 to move into engagement with the inner periphery of backup plate 120, thereby urging anvil head assembly 112 to return to a non-tilted operative position. Additionally, the distal end of stapling device 10 may be configured to engage finger 166 of plunger 154 as anvil assembly 110 is attached to surgical stapling device 10. In this manner, the distal end of surgical stapling device 10 urges plunger 154 distally, thereby ensuring the rotation of anvil head assembly 112 to a non-tilted position.

With particular reference to FIG. 15, in one method, a second incision "$I_2$" is then formed at the surgical site such that distal head portion 16 of surgical stapling device 10 may be received therethrough. Alternatively, distal head portion 16 of surgical stapling device 10 may be received through first incision "$I_1$" once anvil deliver system 50 has been removed therefrom.

Figure 16:
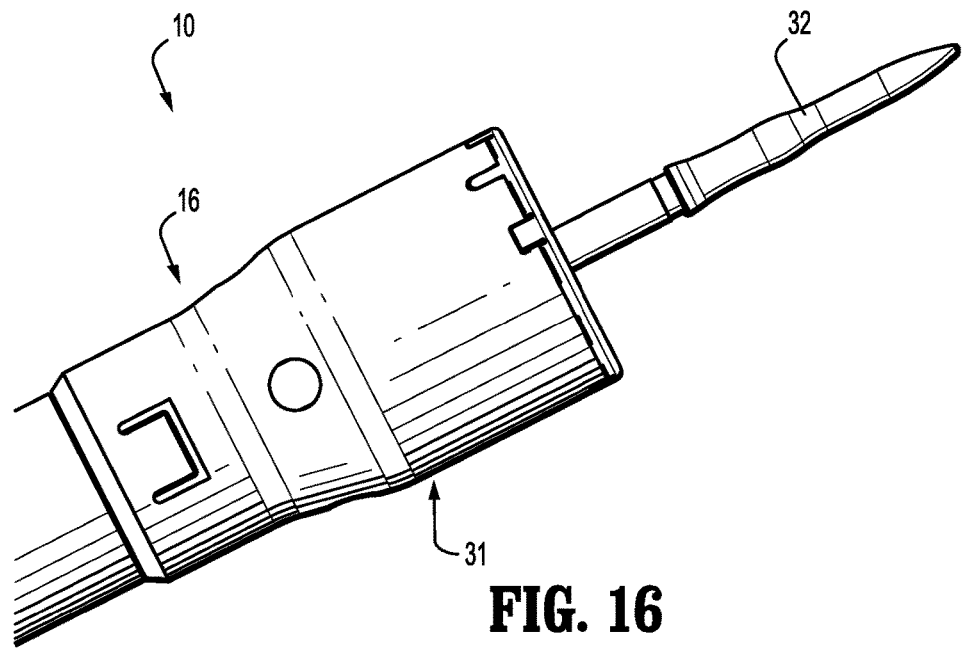
FIG. 16 is an enlarged side view of the distal head portion of the surgical stapling device of FIG. 1 with the anvil assembly removed.
Figure 17:
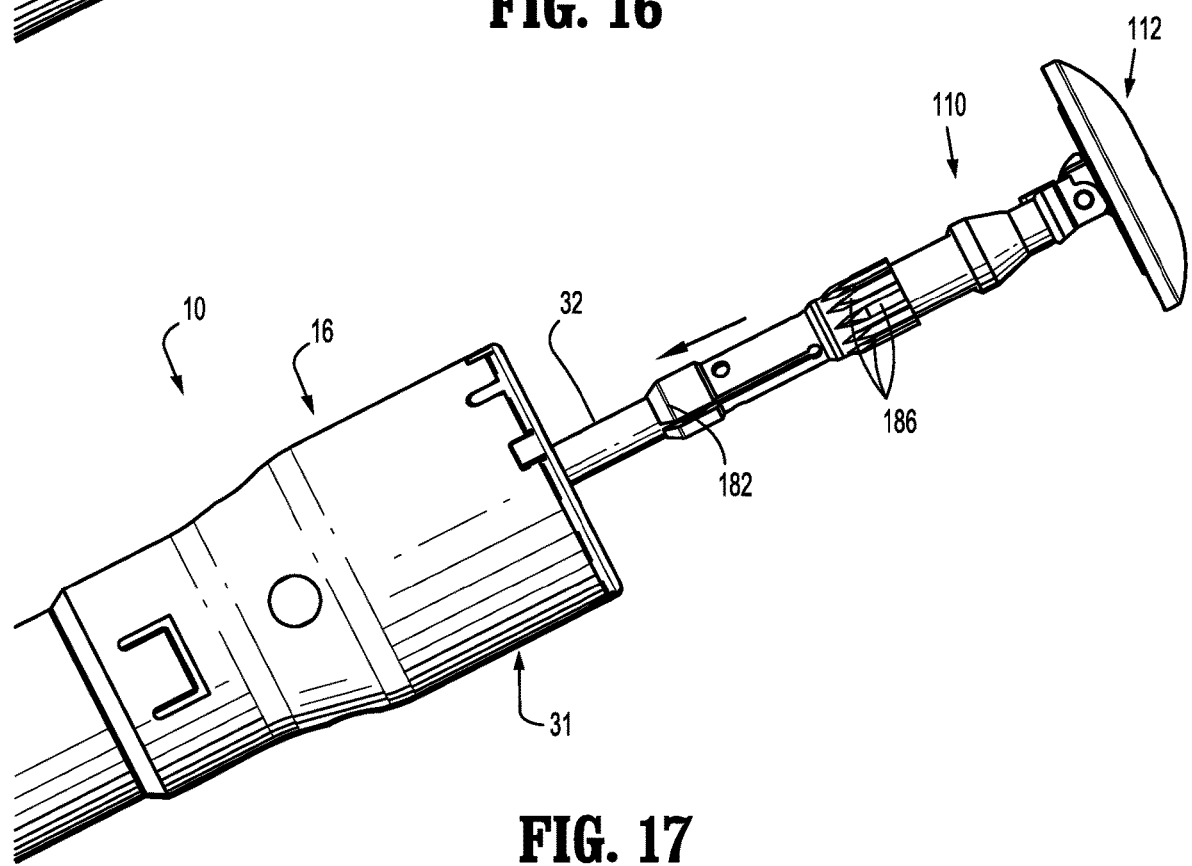
FIG. 17 is an enlarged side view of the distal head portion of the surgical stapling device of FIG. 1 with the anvil assembly of FIGS. 1-7 received thereon.

Turning briefly to FIGS. 16 and 17, anvil assembly 110 is operably received on an anvil retainer 32 extending from shell assembly 31 formed on a distal end of surgical stapling device 10. Once anvil assembly 110 is received on surgical stapling device 10, surgical stapling device 10 operates in the manner discussed in the '060 patent.

The operation of anvil assembly 110 will now be described with reference to FIGS. 18-23. When anvil assembly 110 is in its pre-fired non-tilted position, backup plate 120 is spaced from backwall 118a of housing 118 by retainer 127 and protrusions 152b of center rod 152 engage fingers 138 of backup plate 120 to prevent tilting of anvil head assembly 112 about pivot member 162. Finger 166 of plunger 154 is urged by spring 156 into engagement with body portion 126c of cam latch member 126 to urge cam latch member 126 in a clockwise direction, about pivot member 162 such that edge 126f of cam latch member 126 engages inner periphery 120b of backup member 120.

Figure 22:
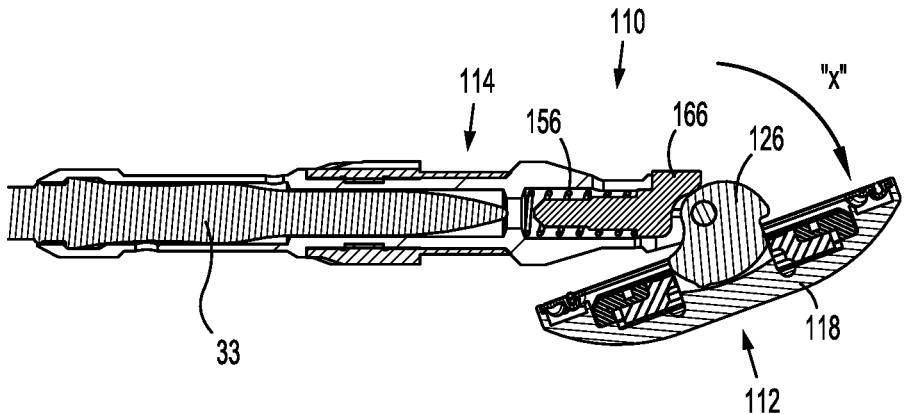
FIG. 22 is a cross-sectional side view of the anvil assembly of FIGS. 1-7 in a post-fired tilted position supported on an anvil retainer of the surgical instrument of FIG. 1.
Figure 22A:
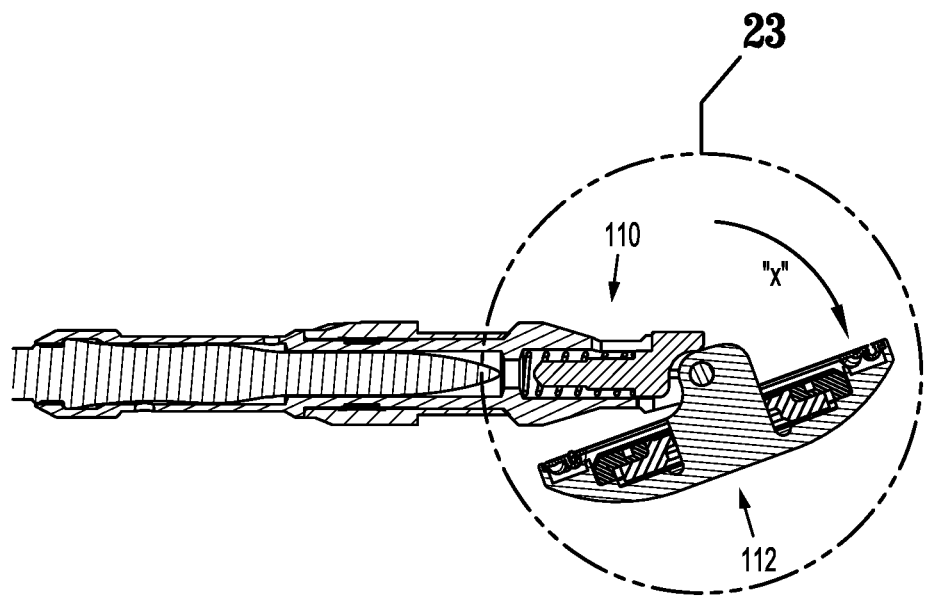
FIG. 22A is another cross-sectional side view of the anvil assembly of FIGS. 1-7 in a post-fired tilted position supported on an anvil retainer of the surgical instrument of FIG. 1
Figure 23:
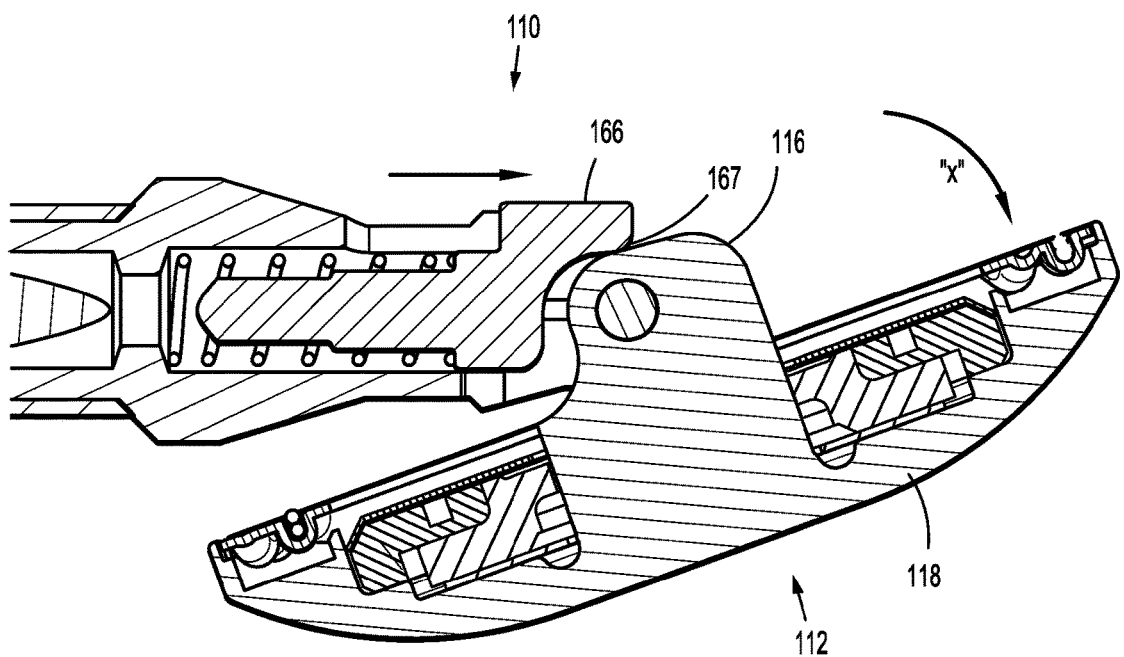
FIG. 23 is an enlarged view of the indicated area of detail shown in FIG. 22A.
Figure 24:
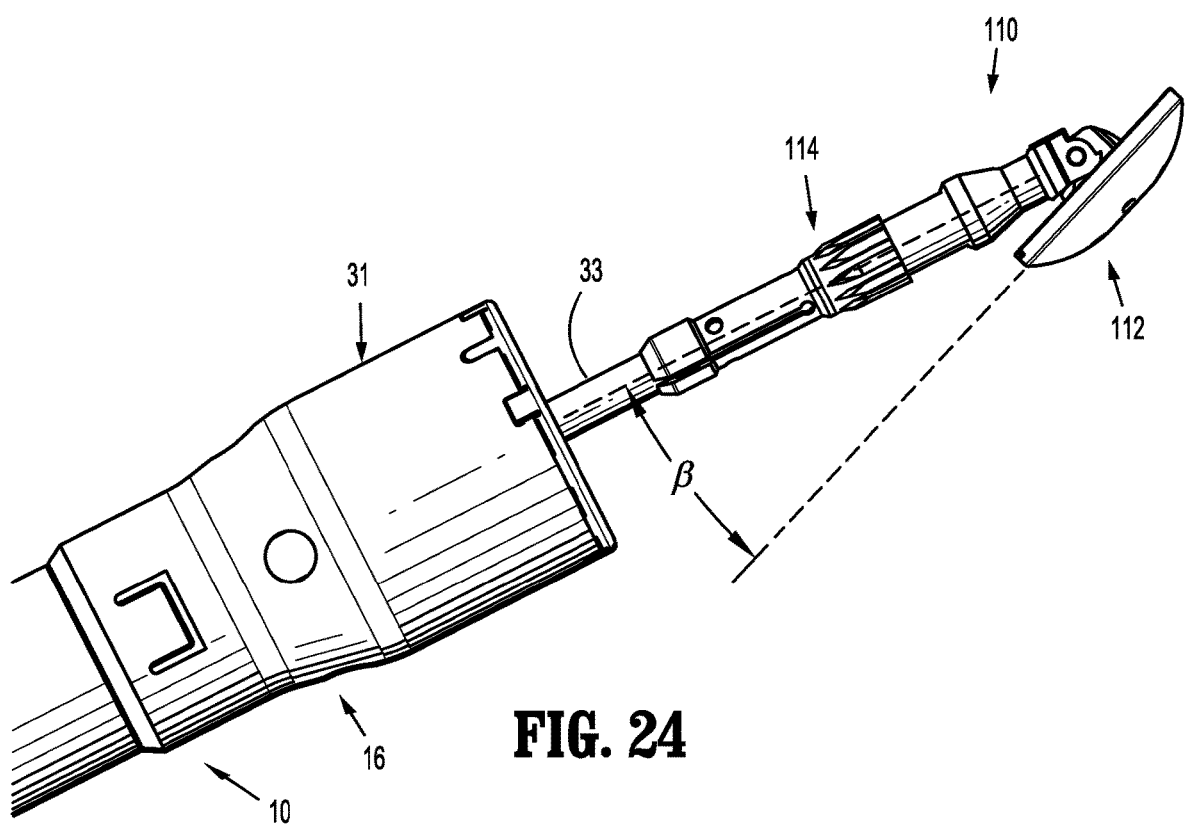
FIG. 24 is a side view of the anvil assembly of FIG. 22 supported on the anvil retainer of the surgical stapling device of FIG. 1.

The firing of surgical stapling device 10 causes a knife blade 33 thereof to engage cutting ring 122 to move cutting ring 122 and backup plate 120 into annular recess 136 of housing 118 of anvil head assembly 112. Arrows "W" in FIG. 19 indicate how cutting ring 122 and backup plate 120 move as a result of the firing of surgical stapling device 10. When such movement occurs, deformable tabs 127a of retainer 127 are deformed against backwall 118a of housing 118 and fingers 138 of backup member 120 move away from protrusions 152b of center rod 152. Further, inner periphery 120b of backup plate 120 moves past edge 126f of cam latch member 126 such that cam latch member 126 is urged to pivot about pivot member 162 in the direction indicated by arrow "X" in FIG. 21 by plunger 154 to a position in which body portion 126d is positioned in front of and engages backup plate 120. Engagement of plunger 154 with cam latch member 126 urges anvil head assembly 112 to a second tilted position (FIGS. 22 and 23). It is noted that anvil head assembly 112 will not immediately tilt upon firing of surgical stapling device 10 because, upon firing, anvil head assembly 112 is in an approximated position, i.e., the anvil head assembly 112 is in close alignment with shell assembly 31 of stapling device 10, and, therefore, does not provide room for head assembly 112 to pivot. As such, the anvil head assembly 112 will only begin to tilt when anvil assembly 110 and shell assembly 31 of surgical stapling device 10 are being unapproximated.

As anvil head assembly 112 pivots towards its forward or second tilted position, finger 166 of plunger 154 maintains surface 126e of cam latch member 126 in contact with backup plate 120 to prevent backup plate 120 from sticking to the knife blade as the knife blade is retracted. It is noted that curved surface 126e of cam latch member is configured to eliminate any gap and ensure contact between surface 126e of cam latch member 126 and backup plate 120 to hold backup plate 120 in place during and after the knife blade is retracted such that the cutting ring and backup plate assembly stay in their correct position during continued tilting of anvil assembly 112. Anvil assembly 110 is configured such that anvil head assembly tilts to a forward or second tilted position β degrees (FIG. 23) relative to center rod assembly 114. In one embodiment, anvil head assembly 112 is tilted about seventy degrees (70°) to its second tilted position such that the total pivoting movement of the anvil from the retracted or first tilted position to the forward or second tilted position is about one-hundred and forty degrees (140°). It should, however, be noted that the tilting of anvil head assembly 112 to other degrees is also contemplated.

As described above, the anvil assemblies of the present disclosure are configured to be delivered to a surgical site, e.g., the stomach "St" (FIG. 15), trans-orally. During transoral delivery of the anvil assemblies, a retaining suture, i.e., first suture "$S_1$", retains the head assembly of the anvil assembly in a first tilted position and a proximal guide suture, i.e., second suture "$S_2$", which includes first and second ends "$S_{2a}$", "$S_{2b}$" that remain external of the patient's mouth "M", permits the surgeon to dislodge or retrieve the anvil assembly 110 from the patient during trans-oral delivery.

As described above and with reference to FIG. 11, second suture "$S_2$" is threaded through openings 119b in housing 118 of head assembly 112 of anvil assembly 110. Detaching second suture "$S_2$" from anvil assembly 110 requires pulling on first end "$S_{2a}$" of second suture "$S_2$" such that second end "$S_{2b}$" of second suture "$S_2$" travels from a location externally of the patient's mouth "M" (FIG. 15) where it is accessible by the surgeon, through the patient's mouth "M" and upper gastrointestinal (GI) tract, e.g., esophagus "E" and stomach "St" (FIG. 15) (collectively referred to as the patient's body lumen) and through the openings 119b in housing 118 of head assembly 112 of anvil assembly 110 before having to travel back through the upper GI tract and out the patient's mouth "M".

With reference now to FIGS. 25-32, an anvil assembly according to alternate embodiment of the present disclosure is shown generally as anvil assembly 210. As will be described in further detail below, the second suture "$S_2$" is secured to anvil assembly 210 in various configurations that permit detaching of the second suture "$S_2$" from the anvil assembly 210 following trans-oral delivery of anvil assembly 210 by pulling on both first and second ends "$S_{2a}$", "$S_{2b}$" of second suture "$S_2$". In this manner, the second end "$S_{2b}$" of second suture "$S_2$" does not travel through the patient's mouth "M" (FIG. 15), upper GI tract, e.g., esophagus "E" (FIG. 15) and stomach "St" (FIG. 15) during withdrawal. The various configurations for securing second suture "$S_2$" to anvil assembly 210 and the methods for securing the second suture "$S_2$" in the various configurations will be described as related to anvil delivery system 50 (FIG. 11) described hereinabove. However, it is envisioned that aspects of the various configurations may be modified for use with various anvil assemblies and anvil delivery systems, and that the anvil assemblies can be used in any of the embodiments disclosed herein, or with any circular stapling apparatus such as robotic, powered, reusable, manual, etc.

Figure 25:
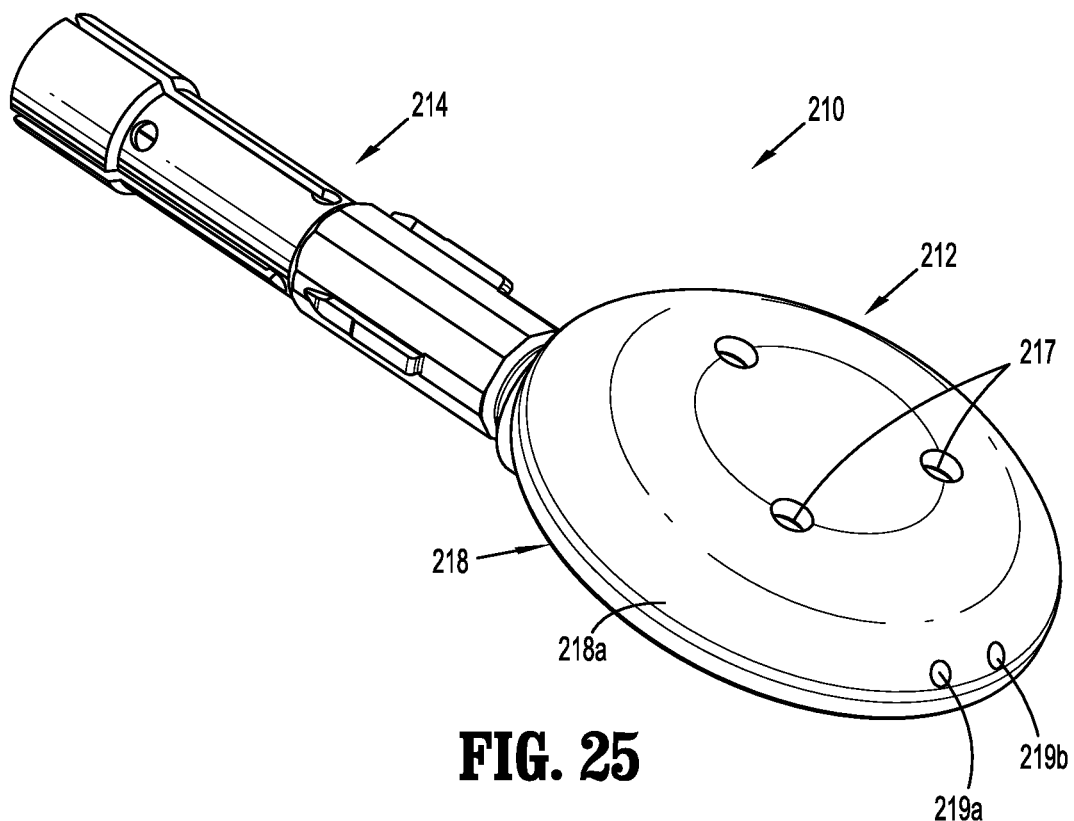
FIG. 25 is a perspective top view of an anvil assembly according to another embodiment of the present disclosure in the first tilted position.
Figure 26:
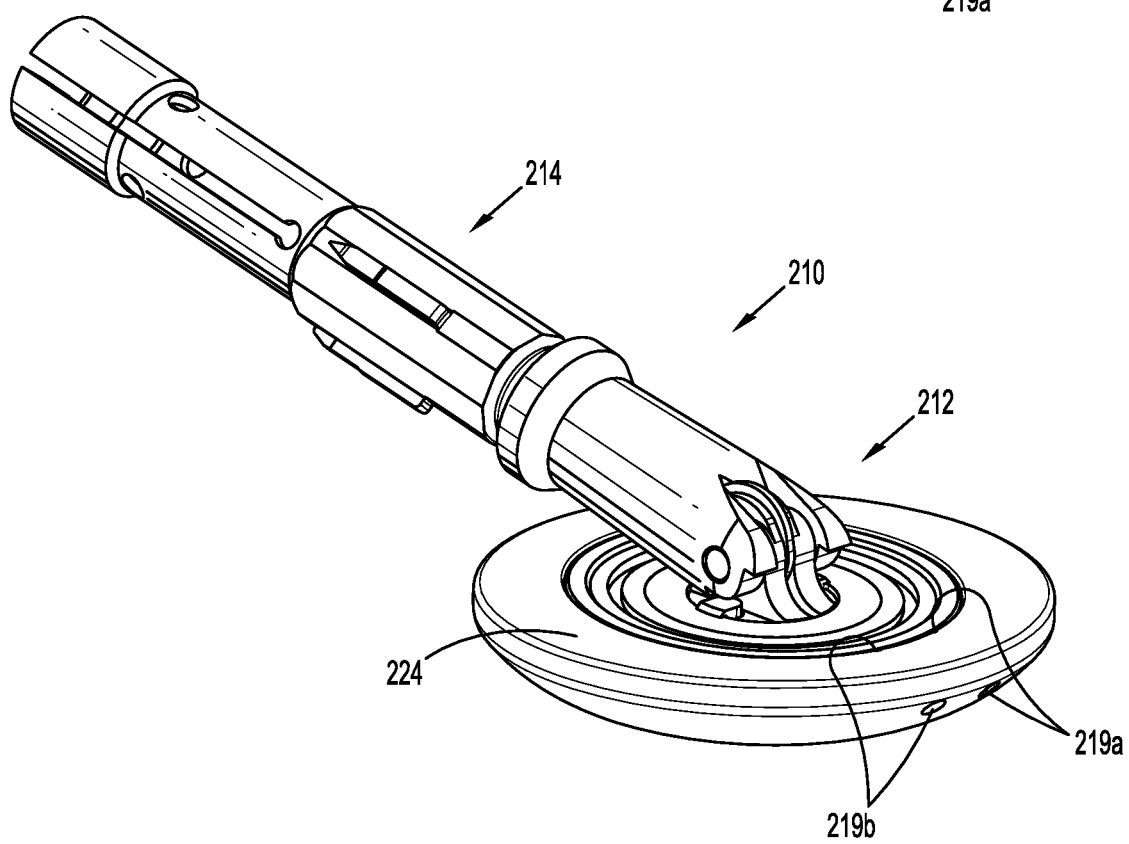
FIG. 26 is a perspective bottom view of the anvil assembly of FIG. 25.
Figure 27:
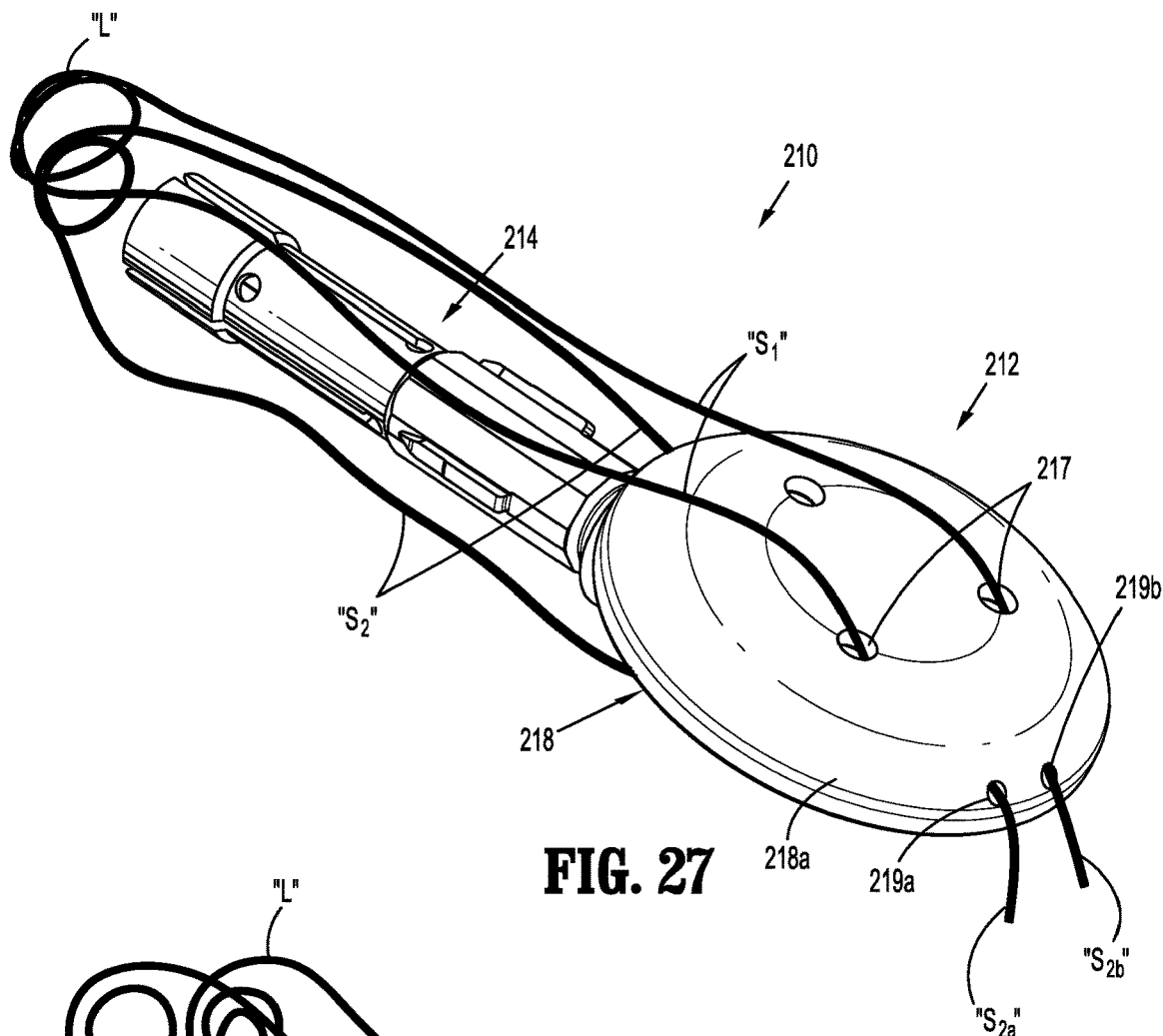
FIG. 27 is a perspective top view of the anvil assembly of FIG. 25 including first and second sutures arranged in a first configuration.

Referring to FIGS. 25 and 26, anvil assembly 210 is substantially similar to anvil assembly 110 (FIG. 2) described hereinabove and includes head assembly 212 and a center rod assembly 214. A housing 218 of head assembly 212 defines a pair of openings 217 for receiving first suture "$S_1$" (FIG. 27). Housing 218 further defines a pair of throughbores 219a, 219b which pass through an outer surface 218a of housing 218 and extend between a cutting ring 222 of head assembly 212 and an anvil plate 224 (staple forming pockets not shown) of head assembly 212. As will be described in further detail below, second suture "$S_2$" may be threaded through either and/or both of throughbores 219a, 219b.

Figure 28:
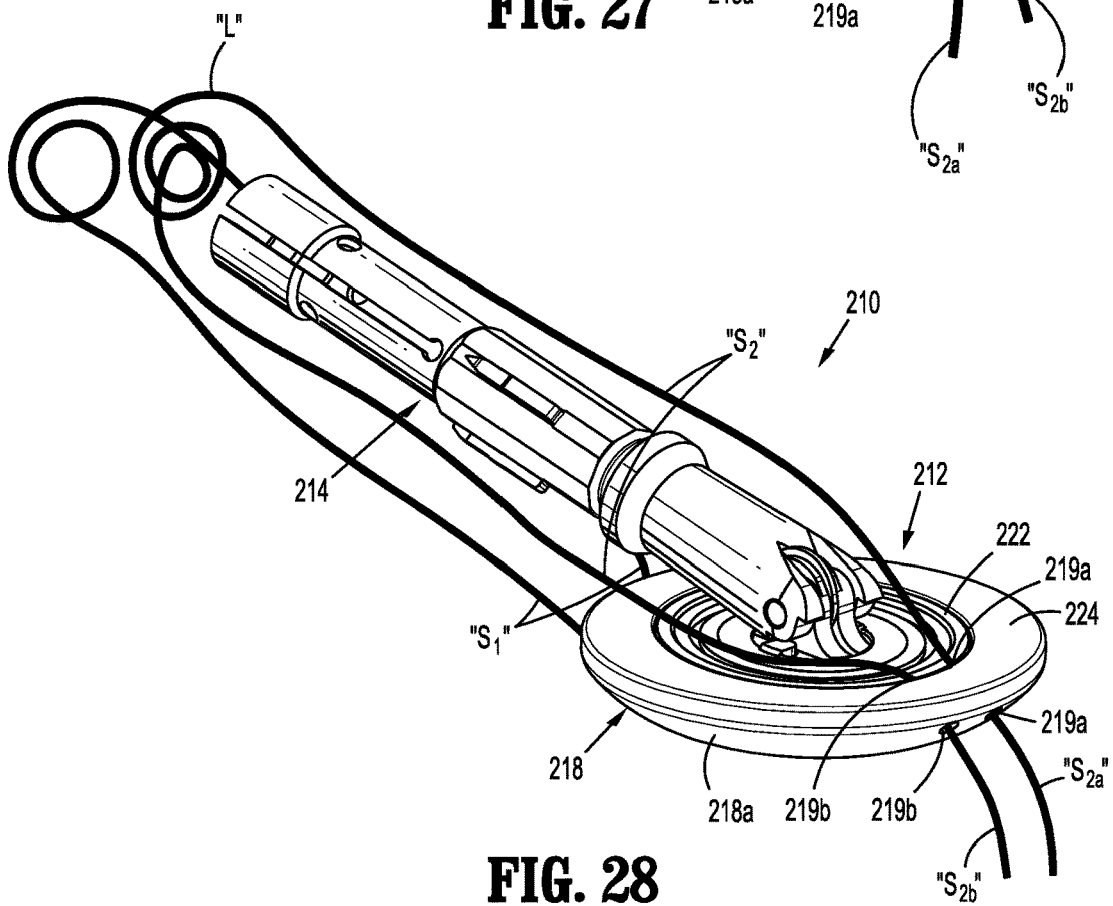
FIG. 28 is a perspective bottom view of the anvil assembly and suture configuration of FIG. 27.

FIGS. 27 and 28 illustrate a first configuration for securing second suture "$S_2$" to anvil assembly 210. In the first configuration, first suture "$S_1$" is received through openings 217 in housing 218 of head assembly 212 of anvil assembly 210 and is secured to anvil delivery system 50 (FIG. 11) as described above and shown in FIGS. 11-13. Briefly, and with reference back to FIG. 13, first and second ends "$S_{1a}$", "$S_{1b}$" of first suture "$S_1$" are received through open end 52a of flexible member 52 of anvil delivery system 50 and through opening 55 formed in flexible member 52. Insertion of the first end 62a of adapter 62 of anvil delivery system 50 into open end 52a of flexible member 52 frictionally secures first and second ends "$S_{1a}$", "$S_{2b}$" of first suture "$S_1$" to anvil delivery system 50. First and second ends "$S_{2a}$", "$S_{2b}$" of second suture "$S_2$" are threaded in a distal direction through respective first and second throughbores 219a, 219b of housing 218 to form a loop "L" at a midpoint of the second suture "$S_2$". The second suture "$S_2$" is secured to anvil delivery system 50 (FIG. 13) by positioning the loop "L" through opening 55 in flexible member 52 and frictionally securing the loop "L" between adapter 62 and flexible member 52.

Although shown as having first end "$S_{2a}$" of second suture "$S_2$" received through first throughbore 219a and a second end "$S_{2b}$" of second suture "$S_2$" received through second throughbore 219b, it is envisioned that both first and second ends "$S_{2a}$", "$S_{2b}$" of second suture "$S_2$" may be received in a distal direction through either of throughbores 219a, 219b or that loop "L" of second suture "$S_2$" may be received in a proximal direction through either of throughbores 219a, 219b. Further, although the second suture "$S_2$" is shown as a single suture having a midpoint secured to the anvil delivery system 50 and first and second ends "$S_{2a}$", "$S_{2b}$" extending distally from anvil assembly 210, it is envisioned that second suture "$S_2$" may include a first end (not shown) extending distally from anvil assembly 210 and a second end (not shown) secured to anvil delivery system 50 (FIG. 13).

Following trans-oral delivery of anvil assembly 210 to a surgical site, e.g., stomach "St" (FIG. 15), first suture "$S_1$"

is cut to allow head assembly 212 of anvil assembly 210 to pivot to a non-tilted or operative position (not shown) as discussed above with respect to anvil assembly 110. When first suture "$S_1$" is cut, second suture "$S_2$" may also be cut to bisect the second suture "$S_2$". Bisecting or cutting the second suture "$S_2$" in half facilitates removal of the second suture "$S_2$" from a patient's body in two pieces which are withdrawn through first and second throughbores 219a, 219b and from within the patient through the patient's mouth "M" (FIG. 15) without first pulling one end of the second suture "$S_2$" through the patient's body lumen.

Figure 29:
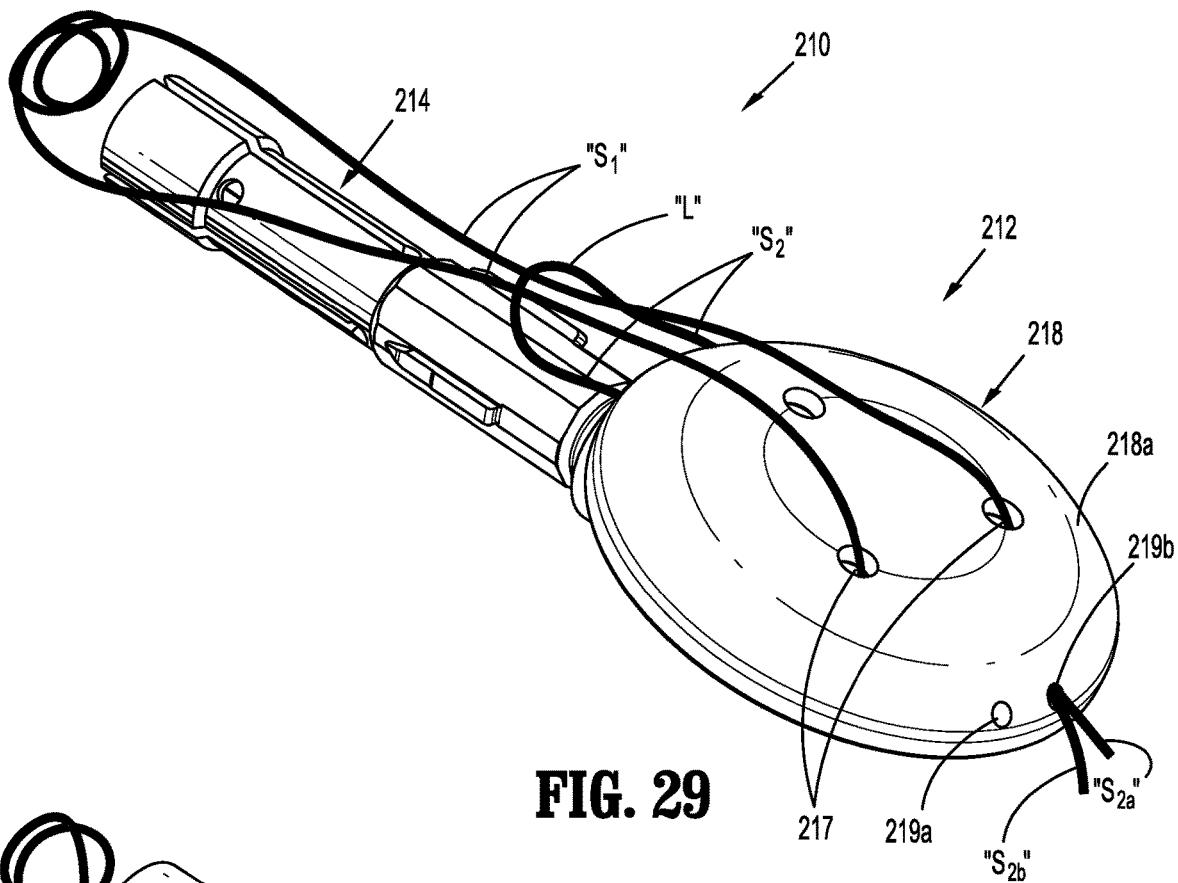
FIG. 29 is a perspective top view of the anvil assembly of FIG. 25 including first and second sutures arranged in a second configuration.
Figure 30:
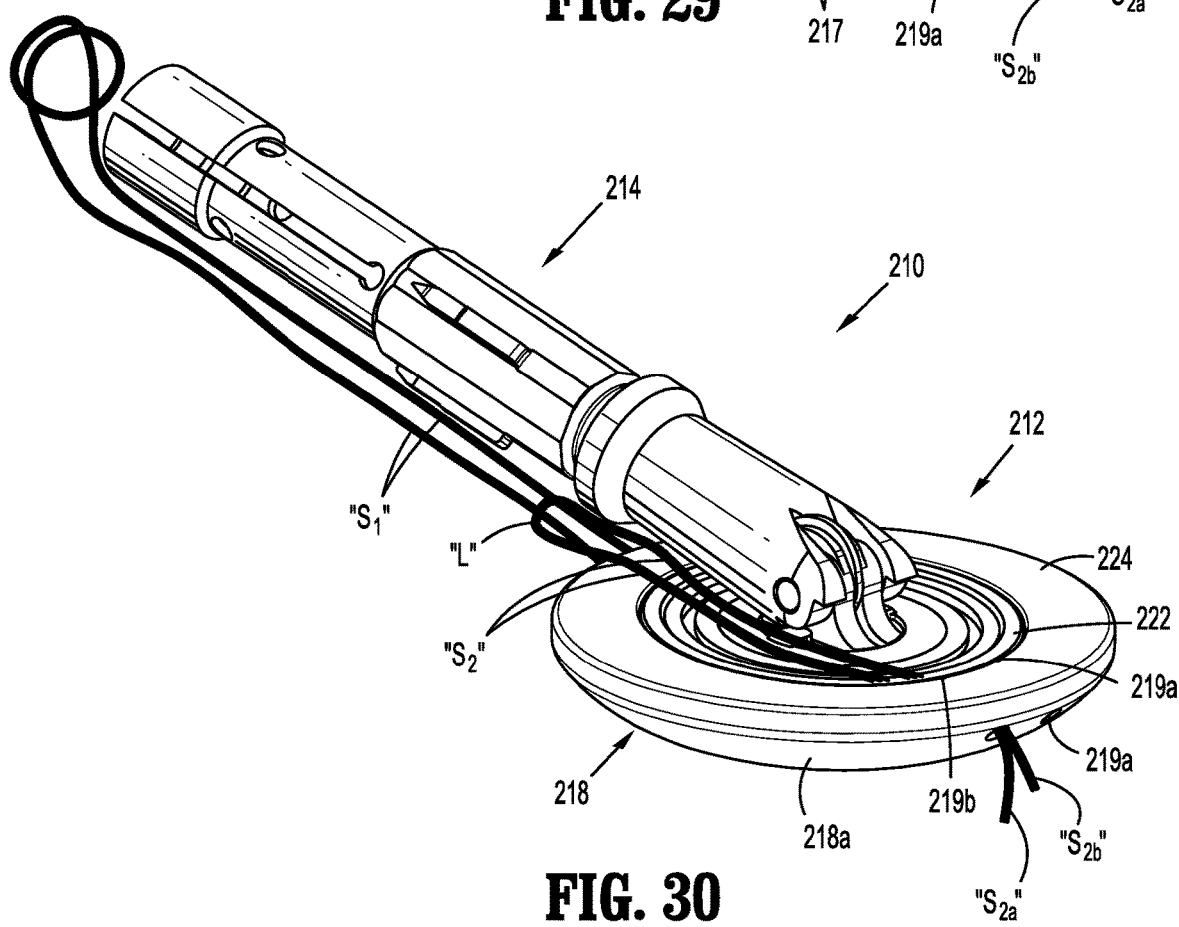
FIG. 30 is a perspective bottom view of the anvil assembly and suture configuration of FIG. 29.

FIGS. 29 and 30 illustrate a second configuration for securing second suture "$S_2$" to anvil assembly 210. A loop "L" formed in second suture "$S_2$" is threaded in a proximal direction through, for example, first or second throughbore 219a, 219b in housing 218 of head assembly 212 of anvil assembly 210. First suture "$S_1$", after being threaded through openings 217 in housing 218 of head assembly 212 of anvil assembly 210, is threaded through the loop "L" in second suture "$S_2$" prior to being secured to anvil delivery system 50 (FIG. 11) as described above. In this manner, second suture "$S_2$" is securely attached to anvil assembly 210 by first suture "$S_1$", i.e., the first suture "$S_1$" is positioned through the loop "L" to prevent removal of the second suture "$S_2$" through the respective throughbore 219a, 219b. Alternatively, after head assembly 212 of anvil assembly 210 is retained in the first tilted position by first suture "$S_1$", a first end "$S_{2a}$" of second suture "$S_2$" is threaded in a proximal direction through first or second throughbore 219a, 219b, wrapped around first suture "$S_1$", and is threaded through first or second throughbore 219a, 219b.

Following trans-oral delivery of anvil assembly 210 to a surgical site, e.g., stomach "St" (FIG. 15), first suture "$S_1$" is cut to allow head assembly 210 to pivot to the non-tilted or operative position (not shown). At this time, first suture "$S_1$" is detachable from head assembly 212 of anvil assembly 210. Detaching first suture "$S_1$" from anvil assembly 210 removes first suture "$S_1$" from within loop "L" of second suture "$S_2$" freeing second suture "$S_2$" to be withdrawn through the respective throughbore 219a, 219b in housing 218 of anvil head assembly and from within the patient directly through the patient's mouth "M" (FIG. 15). Alternatively, loop "L" may be cut by the surgeon to free second suture "$S_2$" prior to cutting first suture "$S_1$".

Figure 31:
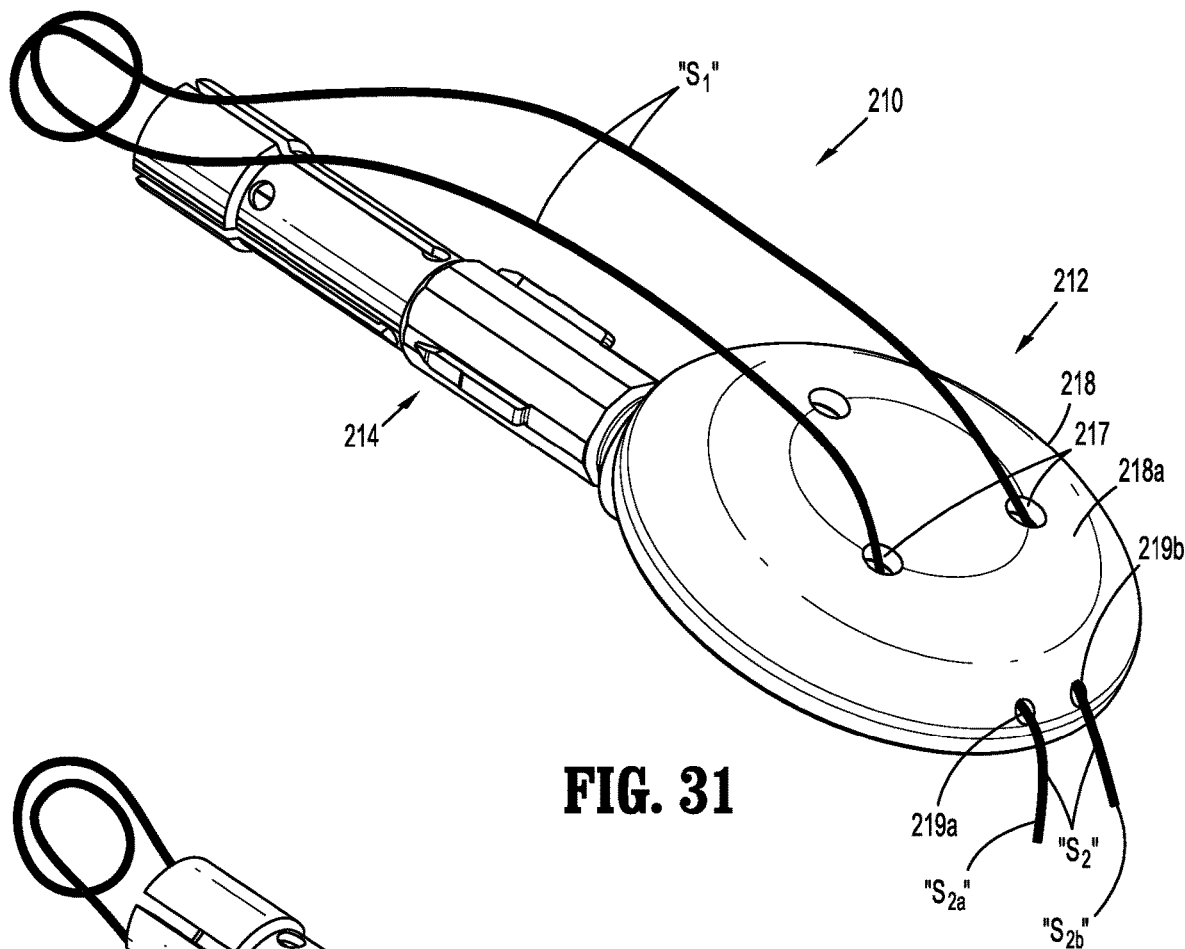
FIG. 31 is a perspective top view of the anvil assembly of FIG. 25 including first and second sutures arranged in a third configuration.
Figure 32:
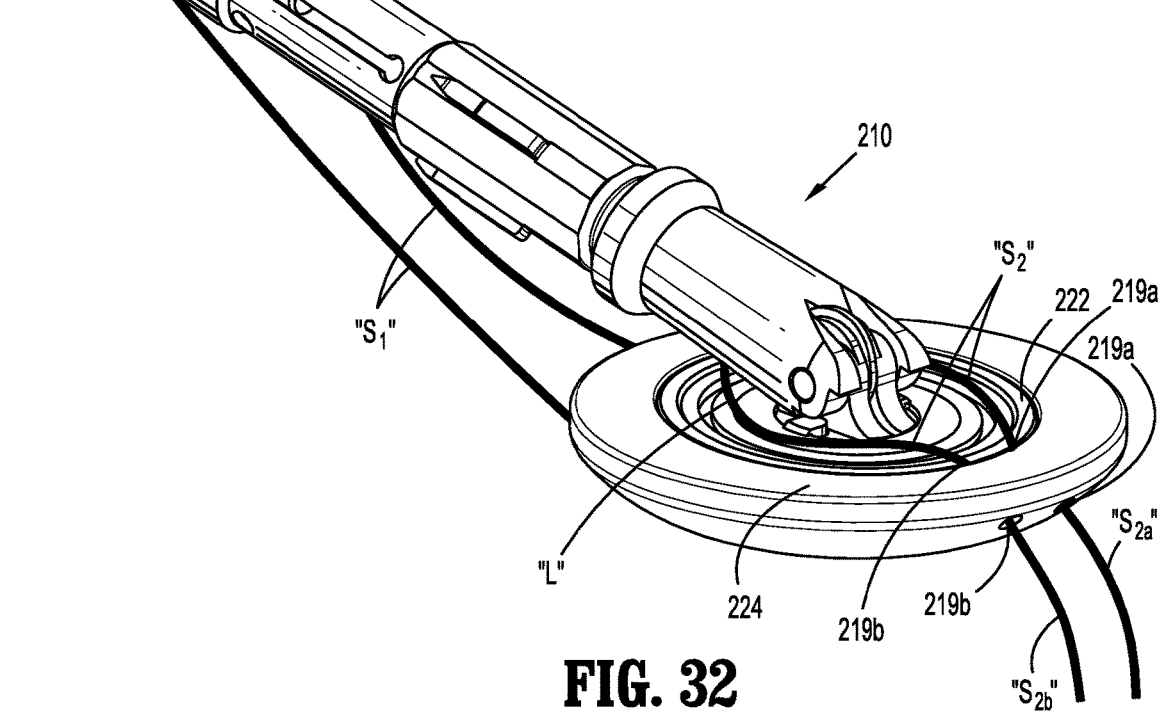
FIG. 32 is a perspective bottom view of the anvil assembly and suture configuration of FIG. 31.

FIGS. 31 and 32 illustrate a third configuration for securing second suture "$S_2$" to anvil assembly 210. The first suture "$S_1$" is secured to anvil delivery system 50 (FIG. 11) in the manner described above to secure head assembly 212 of anvil assembly 210 in the first tilted position. Securing the head assembly 212 in the first tilted position may occur prior to or after securing second suture "$S_2$" to anvil assembly 210.

As shown, a first end "$S_{2a}$" of second suture "$S_2$" is threaded through one of throughbores 219a, 219b, for example, first throughbore 219a, looped around center rod assembly 214 of anvil assembly 210 to form a loop "L", and threaded through second throughbore 219a. Although shown being received through different throughbores 219a, 219b, first and second ends "$S_{2a}$", "$S_{2b}$" of second suture "$S_2$" may be received through the same throughbore 219a, 219b. As shown in FIG. 32, looping second suture "$S_2$" about center rod assembly 214 causes second suture "$S_2$" to cross over cutting ring 222 of head assembly 212 of anvil assembly 210 in two locations.

In an alternative method of securing second suture "$S_2$" to anvil assembly 210 in the third configuration, a loop formed in second suture "$S_2$" is threaded in a proximal direction through one of first or second throughbores 219a, 219b and the loop is received over center rod assembly 214 of anvil assembly 210. After positioning the loop over center rod assembly 214, second suture "$S_2$" is retracted by pulling on first and second ends "$S_{2a}$", "$S_{2b}$" of second suture "$S_2$" to remove the slack in second suture "$S_2$".

Following trans-oral delivery of anvil assembly 210 to a surgical site, e.g., stomach "St" (FIG. 15), anvil assembly 210 is separated from anvil delivery system 50 (FIG. 11) and is secured to stapling device 10 (FIG. 1) in the manner described above. Separation of anvil assembly 210 from anvil delivery system 50 allows head assembly 212 of anvil assembly 210 to pivot to the operative position (FIG. 17). Anvil assembly 210 remains in the operative position during attachment to stapling device 10. In the operative position (not shown), second suture "$S_2$" continues to cross over cutting ring 222 of head assembly 212 of anvil assembly 210.

Firing of stapling device 10 in the manner described above causes knife blade 33 (FIG. 19) of stapling device 10 to advance into engagement with cutting ring 222 of head assembly 212 of anvil assembly 210. Since second suture "$S_2$" crosses over cutting ring 222 in two locations, during firing of stapling device 10 second suture "$S_2$" is severed by knife blade 33 in two locations, resulting in second suture "$S_2$" being cut into three lengths. The length of second suture "$S_2$" received about center rod assembly 214 is removed with the waste tissue cut during the stapling procedure. The remaining portions of second suture "$S_2$" are withdrawn directly through throughbores 219a, 219b and from within the patient by pulling independently on first and second ends "$S_{2a}$", "$S_{2b}$" of second suture "$S_2$".

Thus, the suture can be attached in a way to enable the circular knife to cut the suture to free the suture so that it can be removed. In addition, the suture can be tied so as to facilitate removal of the suture.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. An anvil delivery system comprising:
   a delivery assembly;
   an anvil assembly including:
     a center rod; and
     a head assembly pivotally secured to the center rod about a pivot axis and movable between a first tilted position, an operative position, and a second tilted position, the head assembly defining at least one throughbore;
   a retaining suture secured between the head assembly and the delivery assembly for retaining the head assembly in the first tilted position; and
   a retrieval suture received through the at least one throughbore of the head assembly, the retrieval suture having first and second ends and a loop disposed between the first and second ends, wherein the first and second ends extend distally from the anvil assembly;

wherein the delivery assembly includes a flexible tube and an adapter member and the loop of the retrieval suture is frictionally secured between the flexible tube and the adapter member.

2. An anvil delivery system comprising:
a delivery assembly;
an anvil assembly including:
   a center rod; and
   a head assembly pivotally secured to the center rod about a pivot axis and movable between a first tilted position, an operative position, and a second tilted position, the head assembly defining at least one throughbore;
a retaining suture secured between the head assembly and the delivery assembly for retaining the head assembly in the first tilted position; and
a retrieval suture received through the at least one throughbore of the head assembly, the retrieval suture having first and second ends and a loop disposed between the first and second ends, wherein the first and second ends extend distally from the anvil assembly, and wherein the loop of the retrieval suture is disposed about the retaining suture.

3. An anvil delivery system comprising:
a delivery assembly;
an anvil assembly including:
   a center rod; and
   a head assembly pivotally secured to the center rod about a pivot axis and movable between a first tilted position, an operative position, and a second tilted position, the head assembly defining at least one throughbore;
a retaining suture secured between the head assembly and the delivery assembly for retaining the head assembly in the first tilted position; and
a retrieval suture received through the at least one throughbore of the head assembly, the retrieval suture having first and second ends and a loop disposed between the first and second ends, wherein the first and second ends extend distally from the anvil assembly, and wherein the loop of the retrieval suture is disposed about the center rod.

4. The anvil delivery system of claim 3, wherein the head assembly includes a cutting ring, the retrieval suture extending across the cutting ring when the head assembly is in the operative position.

5. The anvil delivery system of claim 3, wherein the at least one throughbore includes first and second throughbores, the first end of the retrieval suture extending distally from the first througbore and the second end of the retrieval suture extending distally from the second throughbore.

6. An anvil delivery system comprising:
a delivery assembly;
an anvil assembly including:
   a center rod; and
   a head assembly pivotally secured to the center rod about a pivot axis and movable between a first tilted position, an operative position, and a second tilted position, the head assembly defining at least one throughbore;
a retaining suture secured between the head assembly and the delivery assembly for retaining the head assembly in the first tilted position; and
a retrieval suture received through the at least one throughbore of the head assembly, the retrieval suture having first and second ends and a loop disposed between the first and second ends, wherein the first and second ends extend distally from the anvil assembly, and wherein the at least one throughbore includes a first throughbore, the first and second ends of the retrieval suture extending distally from the first throughbore.

7. The anvil delivery system of claim 6, wherein the head assembly is biased towards the second tilted position.

8. An anvil delivery system comprising:
a delivery assembly;
an anvil assembly including:
   a center rod; and
   a head assembly pivotally secured to the center rod about a pivot axis and movable between a first tilted position, an operative position, and a second tilted position, the head assembly defining at least one throughbore;
a retaining suture secured between the head assembly and the delivery assembly for retaining the head assembly in the first tilted position; and
a retrieval suture received through the at least one throughbore of the head assembly, the retrieval suture having first and second ends and a loop disposed between the first and second ends, wherein the first and second ends extend distally from the anvil assembly, wherein the loop of the retrieval suture extends an entire length of the center rod.

9. An anvil delivery system comprising:
a delivery assembly;
an anvil assembly including:
   a center rod; and
   a head assembly pivotally secured to the center rod about a pivot axis and movable between a first tilted position, an operative position, and a second tilted position, the head assembly defining at least one throughbore;
a retaining suture secured between the head assembly and the delivery assembly for retaining the head assembly in the first tilted position; and
a retrieval suture received through the at least one throughbore of the head assembly, the retrieval suture having first and second ends and a loop disposed between the first and second ends, wherein the first and second ends extend distally from the anvil assembly, and wherein the head assembly includes a top surface and a bottom surface, the at least one throughbore extending from the top surface to the bottom surface.

10. The anvil delivery system of claim 9, wherein the anvil assembly is selectively securable to the delivery assembly.

11. An anvil delivery system comprising:
a delivery assembly;
an anvil assembly including:
   a center rod; and
   a head assembly pivotally secured to the center rod about a pivot axis and movable between a first tilted position, an operative position, and a second tilted position, the head assembly defining at least one throughbore; and
a suture received through the at least one throughbore of the head assembly, the suture having first and second ends and a loop disposed between the first and second ends, wherein the first and second ends extend distally from the anvil assembly, wherein the delivery assembly includes a flexible tube and an adapter member, and the loop of the suture is frictionally secured between the flexible tube and the adapter member.

12. An anvil delivery system comprising:
a delivery assembly;

an anvil assembly including:
- a center rod; and
- a head assembly pivotally secured to the center rod about a pivot axis and movable between a first tilted position, an operative position, and a second tilted position, the head assembly defining at least one throughbore; and a suture received through the at least one throughbore of the head assembly, the suture having first and second ends and a loop disposed between the first and second ends, wherein the first and second ends extend distally from the anvil assembly, and wherein the loop of the suture is disposed about the center rod.

13. The anvil delivery system of claim 12, wherein the head assembly includes a cutting ring, the suture extending across the cutting ring when the head assembly is in the operative position.

* * * * *